(12) United States Patent
Almazan

(10) Patent No.: US 9,439,632 B2
(45) Date of Patent: *Sep. 13, 2016

(54) SELF-CONTAINED HANDHELD BIOPSY NEEDLE

(71) Applicant: C. R. Bard, Inc., Tempe, AZ (US)

(72) Inventor: Dan Almazan, Peoria, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/601,342

(22) Filed: Jan. 21, 2015

(65) Prior Publication Data

US 2015/0133814 A1 May 14, 2015

Related U.S. Application Data

(63) Continuation of application No. 12/572,782, filed on Aug. 13, 2012, now Pat. No. 8,951,208, which is a continuation of application No. 12/438,020, filed as application No. PCT/US2007/076214 on Aug. 17, 2007, now Pat. No. 8,251,917.

(60) Provisional application No. 60/823,038, filed on Aug. 21, 2006.

(51) Int. Cl.
*A61B 10/00* (2006.01)
*A61B 10/02* (2006.01)
*A61B 17/00* (2006.01)

(52) U.S. Cl.
CPC .... *A61B 10/0275* (2013.01); *A61B 2010/0208* (2013.01); *A61B 2017/00398* (2013.01); *A61B 2017/00535* (2013.01)

(58) Field of Classification Search
CPC .................. A61B 10/0275; A61B 2010/0208; A61B 1/015; A61B 10/0266; A61B 10/0283; A61B 10/04; A61B 17/320016

USPC ................................................. 600/562–568
See application file for complete search history.

(56) References Cited

U.S. PATENT DOCUMENTS 2,953,934 A 9/1960 Sundt
3,019,733 A 2/1962 Braid
(Continued)

FOREIGN PATENT DOCUMENTS

CN 101011268 A 8/2007
CN 101032420 A 9/2007
(Continued)

OTHER PUBLICATIONS

Merriam-Webster.com, Within—Definition and More from the Free Merriam-Webster Dictionary, downloaded Aug. 15, 2014, 3 pages.
(Continued)

*Primary Examiner* — Rene Towa
*Assistant Examiner* — May Abouelela

(57) ABSTRACT

A method of operating a biopsy device includes inserting a sampling probe having a first component and a second component into a biological tissue mass, the first component having a sample chamber and a side port that opens to the sample chamber, and the second component having a side opening; generating a vacuum in the sample chamber during a first drive interval; rotating at least one of the first component and the second component of the sampling probe during a second drive interval until the side port of the first component and the side opening of the second component are in radial alignment; and rotating at least one of the first component and the second component of the sampling probe during a third drive interval to sever tissue drawn by vacuum into the sample chamber to deposit a tissue sample in the sample chamber.

20 Claims, 12 Drawing Sheets

(56) References Cited

U.S. PATENT DOCUMENTS

| | | |
|---|---|---|
| 3,289,669 A | 12/1966 | Dwyer et al. |
| 3,727,602 A | 4/1973 | Hyden et al. |
| 3,785,380 A | 1/1974 | Brumfield |
| 3,800,783 A | 4/1974 | Jamshidi |
| 3,889,682 A | 6/1975 | Denis et al. |
| 3,916,948 A | 11/1975 | Benjamin |
| 4,282,884 A | 8/1981 | Boebel |
| 4,306,570 A | 12/1981 | Matthews |
| 4,354,092 A | 10/1982 | Manabe et al. |
| 4,393,879 A | 7/1983 | Milgrom |
| 4,445,509 A | 5/1984 | Auth |
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,706,687 A | 11/1987 | Rogers |
| 4,776,346 A | 10/1988 | Beraha et al. |
| 4,792,327 A | 12/1988 | Swartz |
| 4,832,044 A | 5/1989 | Garg |
| 4,844,064 A | 7/1989 | Thimsen et al. |
| 4,907,598 A | 3/1990 | Bauer |
| RE33,258 E | 7/1990 | Onik et al. |
| 4,952,817 A | 8/1990 | Bolan et al. |
| 5,048,538 A | 9/1991 | Terwilliger et al. |
| 5,057,822 A | 10/1991 | Hoffman |
| 5,078,603 A | 1/1992 | Cohen |
| 5,138,245 A | 8/1992 | Mattinger et al. |
| 5,146,921 A | 9/1992 | Terwilliger et al. |
| 5,156,160 A | 10/1992 | Bennett |
| 5,158,528 A | 10/1992 | Walker et al. |
| 5,172,702 A | 12/1992 | Leigh et al. |
| 5,183,052 A | 2/1993 | Terwilliger |
| 5,197,484 A | 3/1993 | Kornberg et al. |
| 5,223,012 A | 6/1993 | Best et al. |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,290,253 A | 3/1994 | Kira |
| 5,334,183 A | 8/1994 | Wuchinich |
| 5,335,671 A | 8/1994 | Clement |
| 5,383,874 A | 1/1995 | Jackson et al. |
| 5,397,462 A | 3/1995 | Higashijima et al. |
| 5,471,994 A | 12/1995 | Guirguis |
| 5,479,486 A | 12/1995 | Saji |
| 5,485,917 A | 1/1996 | Early |
| 5,492,130 A | 2/1996 | Chiou |
| 5,526,822 A | 6/1996 | Burbank et al. |
| 5,535,755 A | 7/1996 | Heske |
| 5,554,151 A | 9/1996 | Hinchliffe |
| 5,569,284 A | 10/1996 | Young et al. |
| 5,575,293 A | 11/1996 | Miller et al. |
| 5,591,170 A | 1/1997 | Spievack et al. |
| 5,601,583 A | 2/1997 | Donahue et al. |
| 5,601,585 A | 2/1997 | Banik et al. |
| 5,612,738 A | 3/1997 | Kim |
| 5,655,657 A | 8/1997 | Roshdy |
| 5,669,394 A | 9/1997 | Bergey et al. |
| 5,699,909 A | 12/1997 | Foster |
| 5,700,265 A | 12/1997 | Romano |
| 5,735,264 A | 4/1998 | Siczek et al. |
| 5,755,714 A | 5/1998 | Murphy-Chutorian |
| 5,769,086 A | 6/1998 | Ritchart et al. |
| 5,779,649 A | 7/1998 | Herbert |
| 5,830,219 A | 11/1998 | Bird et al. |
| 5,871,699 A | 2/1999 | Ruggeri |
| 5,879,365 A | 3/1999 | Whitfield et al. |
| 5,908,233 A | 6/1999 | Heskett et al. |
| 5,916,198 A | 6/1999 | Dillow |
| 5,916,229 A | 6/1999 | Evans |
| 5,928,164 A | 7/1999 | Burbank et al. |
| 5,951,575 A | 9/1999 | Bolduc et al. |
| 5,980,545 A | 11/1999 | Pacala et al. |
| 6,018,227 A | 1/2000 | Kumar et al. |
| 6,022,325 A | 2/2000 | Siczek et al. |
| 6,055,870 A | 5/2000 | Jaeger |
| 6,071,247 A | 6/2000 | Kennedy |
| 6,086,544 A | 7/2000 | Hibner et al. |
| 6,120,462 A | 9/2000 | Hibner et al. |
| 6,123,957 A | 9/2000 | Jernberg |
| 6,220,248 B1 | 4/2001 | Voegele et al. |
| 6,267,759 B1 | 7/2001 | Quick |
| 6,273,862 B1 | 8/2001 | Privitera et al. |
| 6,331,166 B1 | 12/2001 | Burbank et al. |
| 6,358,217 B1 | 3/2002 | Bourassa |
| 6,419,641 B1 | 7/2002 | Mark et al. |
| 6,434,507 B1 | 8/2002 | Clayton et al. |
| 6,461,302 B1 | 10/2002 | Thompson |
| 6,471,659 B2 | 10/2002 | Eggers et al. |
| 6,482,158 B2 | 11/2002 | Mault |
| 6,494,844 B1 | 12/2002 | Van Bladel et al. |
| 6,527,736 B1 | 3/2003 | Attinger et al. |
| 6,544,194 B1 | 4/2003 | Kortenbach et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,626,849 B2 | 9/2003 | Huitema et al. |
| 6,632,182 B1 | 10/2003 | Treat |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,832,990 B2 | 12/2004 | Kortenbach et al. |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 7,004,174 B2 | 2/2006 | Eggers et al. |
| 7,010,332 B1 | 3/2006 | Irvin et al. |
| D525,583 S | 7/2006 | Vu |
| 7,108,660 B2 | 9/2006 | Stephens et al. |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,322 B2 | 4/2009 | Weikel, Jr. et al. |
| 7,549,978 B2 | 6/2009 | Carlson et al. |

(56) References Cited

U.S. PATENT DOCUMENTS

| | | |
|---|---|---|
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,806,834 B2 | 10/2010 | Beckman et al. |
| 7,828,746 B2 | 11/2010 | Teague |
| 7,828,747 B2 | 11/2010 | Heske et al. |
| 7,846,109 B2 | 12/2010 | Parihar et al. |
| 7,854,706 B2 | 12/2010 | Hibner |
| 7,862,517 B2 | 1/2011 | Tsonton et al. |
| 7,862,518 B2 | 1/2011 | Parihar |
| 7,871,384 B2 | 1/2011 | Thompson et al. |
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,959,580 B2 | 6/2011 | Mccullough et al. |
| 7,974,681 B2 | 7/2011 | Wallace et al. |
| 8,002,713 B2 | 8/2011 | Heske et al. |
| 8,012,102 B2 | 9/2011 | McCullough et al. |
| 8,016,772 B2 | 9/2011 | Heske et al. |
| 8,016,844 B2 | 9/2011 | Privitera et al. |
| 8,052,614 B2 | 11/2011 | Heske et al. |
| 8,052,615 B2 | 11/2011 | Reuber et al. |
| 8,057,402 B2 | 11/2011 | Hibner et al. |
| 8,073,008 B2 | 12/2011 | Mehta et al. |
| 8,075,495 B2 | 12/2011 | Andreyko et al. |
| 8,083,671 B2 | 12/2011 | Boulais et al. |
| 8,083,687 B2 | 12/2011 | Parihar |
| 8,109,885 B2 | 2/2012 | Heske et al. |
| 8,118,755 B2 | 2/2012 | Hibner et al. |
| 8,152,738 B2 | 4/2012 | Li et al. |
| 8,157,744 B2 | 4/2012 | Jorgensen et al. |
| 8,162,851 B2 | 4/2012 | Heske et al. |
| 8,172,771 B2 | 5/2012 | Miller et al. |
| 8,172,773 B2 | 5/2012 | Heske et al. |
| 8,187,204 B2 | 5/2012 | Miller et al. |
| 8,190,238 B2 | 5/2012 | Moll et al. |
| 8,206,409 B2 | 6/2012 | Privitera et al. |
| 8,251,917 B2 | 8/2012 | Almazan |
| 8,262,585 B2 | 9/2012 | Thompson et al. |
| 8,262,586 B2 | 9/2012 | Anderson et al. |
| 8,267,868 B2 | 9/2012 | Taylor et al. |
| 8,277,393 B2 | 10/2012 | Miller et al. |
| 8,282,574 B2 | 10/2012 | Coonahan et al. |
| 8,283,890 B2 | 10/2012 | Videbaek |
| 8,287,465 B2 | 10/2012 | Hardin et al. |
| 8,313,444 B2 | 11/2012 | Thompson et al. |
| 8,343,069 B2 | 1/2013 | Uchiyama et al. |
| 8,366,636 B2 | 2/2013 | Videbaek |
| 8,430,824 B2 | 4/2013 | Videbaek et al. |
| 8,430,825 B2 | 4/2013 | Mark |
| 8,430,827 B2 | 4/2013 | Nicoson et al. |
| 8,485,987 B2 | 7/2013 | Videbaek et al. |
| 8,485,989 B2 | 7/2013 | Videbaek |
| 8,702,621 B2 | 4/2014 | Mccullough et al. |
| 8,702,622 B2 | 4/2014 | McCullough et al. |
| 8,721,563 B2 | 5/2014 | Taylor et al. |
| 8,728,003 B2 | 5/2014 | Taylor et al. |
| 8,728,004 B2 | 5/2014 | Heske et al. |
| 8,771,200 B2 | 7/2014 | Thompson et al. |
| 8,864,680 B2 | 10/2014 | Videbæk et al. |
| 8,926,527 B2 | 1/2015 | Jørgensen et al. |
| 8,951,208 B2 * | 2/2015 | Almazan ............ A61B 10/0275 600/566 |
| 8,956,306 B2 | 2/2015 | Hibner |
| 2001/0011156 A1 | 8/2001 | Viola et al. |
| 2002/0029007 A1 | 3/2002 | Bryan et al. |
| 2002/0045840 A1 | 4/2002 | Voegele et al. |
| 2002/0065474 A1 | 5/2002 | Viola |
| 2002/0067151 A1 | 6/2002 | Tanishita |
| 2002/0107043 A1 | 8/2002 | Adamson et al. |
| 2002/0115942 A1 | 8/2002 | Stanford et al. |
| 2002/0143269 A1 | 10/2002 | Neuenfeldt |
| 2002/0151822 A1 | 10/2002 | Burdorff et al. |
| 2003/0023188 A1 | 1/2003 | Kritzman et al. |
| 2003/0023239 A1 | 1/2003 | Burbank et al. |
| 2003/0073929 A1 | 4/2003 | Baltschun et al. |
| 2003/0093103 A1 | 5/2003 | Malackowski et al. |
| 2003/0163142 A1 | 8/2003 | Paltieli et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0034280 A1 | 2/2004 | Privitera et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0162505 A1 | 8/2004 | Kaplan et al. |
| 2004/0167428 A1 | 8/2004 | Quick et al. |
| 2004/0210161 A1 | 10/2004 | Burdorff et al. |
| 2004/0220495 A1 | 11/2004 | Cahir et al. |
| 2004/0230135 A1 | 11/2004 | Merkle |
| 2005/0004559 A1 | 1/2005 | Quick et al. |
| 2005/0020909 A1 | 1/2005 | Moctezuma de la Barrera et al. |
| 2005/0054947 A1 | 3/2005 | Goldenberg |
| 2005/0065453 A1 | 3/2005 | Shabaz et al. |
| 2005/0080355 A1 | 4/2005 | Mark |
| 2005/0088120 A1 | 4/2005 | Avis |
| 2005/0113715 A1 | 5/2005 | Schwindt et al. |
| 2005/0113716 A1 | 5/2005 | Mueller, Jr. et al. |
| 2005/0124915 A1 | 6/2005 | Eggers et al. |
| 2005/0165328 A1 | 7/2005 | Heske et al. |
| 2005/0165329 A1 | 7/2005 | Taylor et al. |
| 2005/0193451 A1 | 9/2005 | Quistgaard et al. |
| 2005/0203439 A1 | 9/2005 | Heske et al. |
| 2005/0215921 A1 | 9/2005 | Hibner et al. |
| 2005/0275378 A1 | 12/2005 | Canino et al. |
| 2005/0288605 A1 | 12/2005 | Pellegrino et al. |
| 2006/0030784 A1 | 2/2006 | Miller et al. |
| 2006/0074350 A1 | 4/2006 | Cash |
| 2006/0113958 A1 | 6/2006 | Lobert et al. |
| 2006/0116603 A1 | 6/2006 | Shibazaki et al. |
| 2006/0122535 A1 | 6/2006 | Daum |
| 2006/0149162 A1 | 7/2006 | Daw et al. |
| 2006/0173377 A1 | 8/2006 | McCullough et al. |
| 2006/0260994 A1 | 11/2006 | Mark et al. |
| 2007/0027407 A1 | 2/2007 | Miller |
| 2007/0032743 A1 | 2/2007 | Hibner |
| 2007/0055173 A1 | 3/2007 | DeLonzor et al. |
| 2007/0090788 A1 | 4/2007 | Hansford et al. |
| 2007/0118048 A1 | 5/2007 | Stephens et al. |
| 2007/0118049 A1 | 5/2007 | Viola |
| 2007/0123797 A1 | 5/2007 | Krause |
| 2007/0149894 A1 | 6/2007 | Heske et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0276288 A1 | 11/2007 | Khaw |
| 2007/0287933 A1 | 12/2007 | Phan et al. |
| 2007/0292858 A1 | 12/2007 | Chen et al. |
| 2007/0293788 A1 | 12/2007 | Entrekin et al. |
| 2007/0293830 A1 | 12/2007 | Martin |
| 2008/0007217 A1 | 1/2008 | Riley |
| 2008/0015429 A1 | 1/2008 | Tsonton et al. |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |

(56) References Cited

U.S. PATENT DOCUMENTS

| | | |
|---|---|---|
| 2008/0079391 A1 | 4/2008 | Schroeck et al. |
| 2008/0103411 A1 | 5/2008 | Van Bladel et al. |
| 2008/0125634 A1 | 5/2008 | Ryan et al. |
| 2008/0135443 A1 | 6/2008 | Frojd et al. |
| 2008/0146965 A1 | 6/2008 | Privitera et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0200833 A1 | 8/2008 | Hardin et al. |
| 2008/0200836 A1 | 8/2008 | Speeg et al. |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0228104 A1 | 9/2008 | Uber et al. |
| 2008/0232604 A1 | 9/2008 | Dufresne et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0015208 A1 | 1/2009 | White et al. |
| 2009/0030405 A1 | 1/2009 | Quick et al. |
| 2009/0048532 A1 | 2/2009 | Stephens et al. |
| 2009/0048533 A1 | 2/2009 | Miller |
| 2009/0062624 A1 | 3/2009 | Neville |
| 2009/0082695 A1 | 3/2009 | Whitehead |
| 2009/0087249 A1 | 4/2009 | Flagle et al. |
| 2009/0088666 A1 | 4/2009 | Miller et al. |
| 2009/0112118 A1 | 4/2009 | Quick, Jr. et al. |
| 2009/0125062 A1 | 5/2009 | Arnin |
| 2009/0137927 A1 | 5/2009 | Miller |
| 2009/0171242 A1 | 7/2009 | Hibner |
| 2009/0171243 A1 | 7/2009 | Hibner et al. |
| 2009/0204022 A1 | 8/2009 | Schwindt |
| 2009/0227893 A1 | 9/2009 | Coonahan et al. |
| 2009/0281453 A1 | 11/2009 | Tsonton et al. |
| 2010/0030020 A1 | 2/2010 | Sanders et al. |
| 2010/0030108 A1 | 2/2010 | Anderson et al. |
| 2010/0106053 A1 | 4/2010 | Videbaek et al. |
| 2010/0152610 A1 | 6/2010 | Parihar et al. |
| 2010/0152611 A1 | 6/2010 | Parihar et al. |
| 2010/0160820 A1 | 6/2010 | Weikel, Jr. et al. |
| 2010/0160823 A1 | 6/2010 | Parihar et al. |
| 2010/0210966 A1 | 8/2010 | Videbaek |
| 2010/0222700 A1 | 9/2010 | Hibner |
| 2010/0234760 A1 | 9/2010 | Almazan |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2010/0324449 A1 | 12/2010 | Rostaing et al. |
| 2011/0004119 A1 | 1/2011 | Hoffa et al. |
| 2011/0021946 A1 | 1/2011 | Heske et al. |
| 2011/0054350 A1 | 3/2011 | Videbaek |
| 2011/0077551 A1 | 3/2011 | Videbaek |
| 2011/0087131 A1 | 4/2011 | Videbaek |
| 2011/0105945 A1 | 5/2011 | Videbaek et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |
| 2011/0208085 A1 | 8/2011 | Mccullough et al. |
| 2011/0224577 A1 | 9/2011 | Park |
| 2011/0295150 A1 | 12/2011 | Mccullough et al. |
| 2012/0071787 A1 | 3/2012 | Reuber et al. |
| 2012/0095366 A1 | 4/2012 | Heske et al. |
| 2012/0130275 A1 | 5/2012 | Chudzik et al. |
| 2012/0184873 A1 | 7/2012 | Jorgensen et al. |
| 2012/0191009 A1 | 7/2012 | Hoon et al. |
| 2012/0203135 A1 | 8/2012 | Heske et al. |
| 2012/0215130 A1 | 8/2012 | Field et al. |
| 2012/0238905 A1 | 9/2012 | Heske et al. |
| 2012/0310109 A1 | 12/2012 | Almazan |
| 2012/0323120 A1 | 12/2012 | Taylor et al. |
| 2012/0323140 A1 | 12/2012 | Taylor et al. |
| 2012/0330185 A1 | 12/2012 | Coonahan et al. |
| 2013/0023789 A1 | 1/2013 | Anderson et al. |
| 2013/0023791 A1 | 1/2013 | Thompson et al. |
| 2013/0289441 A1 | 10/2013 | Videbaek et al. |
| 2014/0228706 A1 | 8/2014 | Mccullough et al. |
| 2014/0371585 A1 | 12/2014 | Thompson et al. |
| 2015/0025415 A1 | 1/2015 | Videbaek et al. |
| 2015/0094613 A1 | 4/2015 | Jorgensen et al. |
| 2015/0148702 A1 | 5/2015 | Heske et al. |
| 2015/0190124 A1 | 7/2015 | Mccullough et al. |
| 2015/0238174 A1 | 8/2015 | Reuber et al. |

FOREIGN PATENT DOCUMENTS

| | | |
|---|---|---|
| DE | 3924291 A1 | 1/1991 |
| DE | 3924291 C2 | 7/2000 |
| DE | 20204363 U1 | 5/2002 |
| DE | 10235480 A1 | 2/2004 |
| EP | 0890339 A1 | 1/1999 |
| EP | 1604615 A1 | 12/2005 |
| EP | 1665989 A2 | 6/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| GB | 2323288 A | 9/1998 |
| JP | 1-126957 A | 9/1987 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9734531 A1 | 9/1997 |
| WO | 9831285 A1 | 7/1998 |
| WO | 9846290 A1 | 10/1998 |
| WO | 9933501 A1 | 7/1999 |
| WO | 0004832 A1 | 2/2000 |
| WO | 2006005342 A1 | 1/2006 |
| WO | 2007047128 A1 | 4/2007 |
| WO | 2008021687 A1 | 2/2008 |
| WO | 2008131362 A2 | 10/2008 |
| WO | 2010107424 A1 | 9/2010 |
| WO | 2010120294 A1 | 10/2010 |
| WO | 2011019343 A1 | 2/2011 |

OTHER PUBLICATIONS

Merriam-Webster.com, Series—Definition and More from the Free Merriam-Webster Dictionary, downloaded Aug. 15, 2014, 3 pages.

Merriam-Webster.com, Restrain—Definition and More from the Free Merriam-Webster Dictionary, downloaded Aug. 17, 2014, 3 pages.

Merriam-Webster.com, While—Definition and More from the Free Merriam-Webster Dictionary, downloaded Aug. 17, 2014, 4 pages.

Maxim; Maxim8606; USB/AC Adapter, Li+ Linear Battery Charger with Integrated 50m Omega Battery Switch in TDFN; http://datasheets.maxim-ic.com/en/ds/MAX8606.pdf; Dec. 2008; pp. 1-14; Rev 1.

\* cited by examiner

A-A

B-B

A-A

B-B

A-A

B-B

A-A

B-B

A-A

B-B

C-C

D-D

C-C

D-D

C-C

D-D

C-C

D-D

C-C

D-D

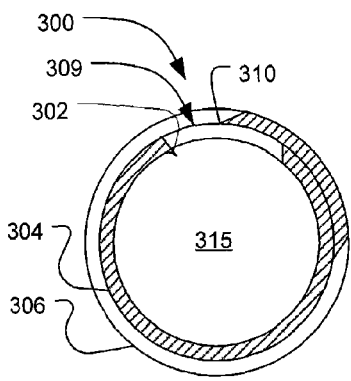
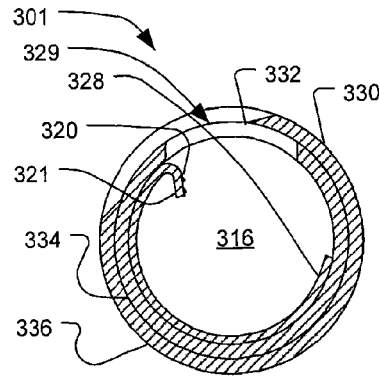
Fig. 5A  Fig. 5B
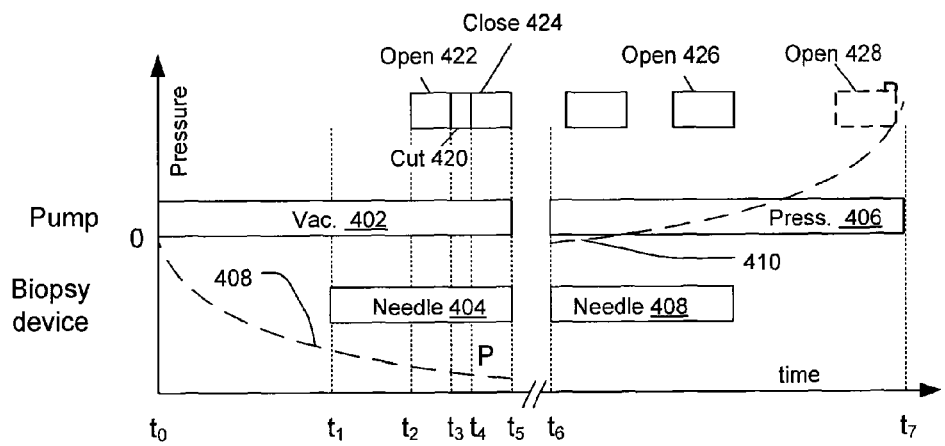
Fig. 6A
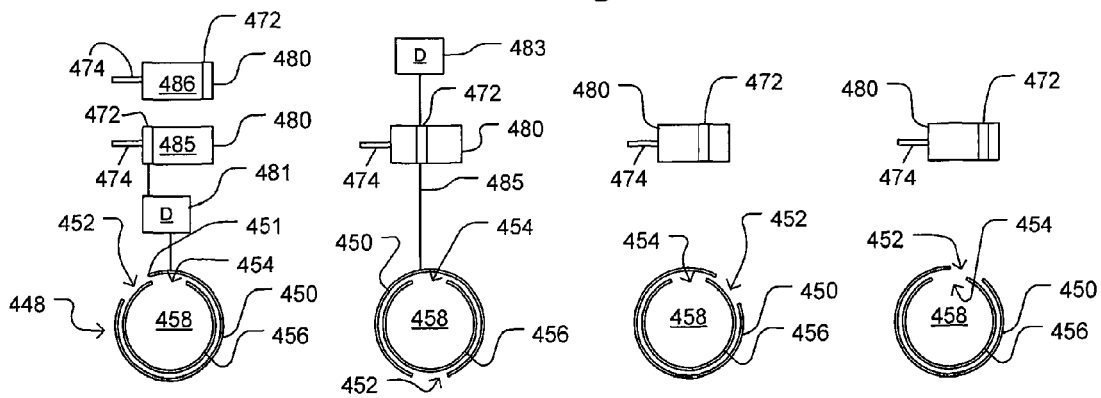
Fig. 6B  Fig. 6C  Fig. 6D  Fig. 6E

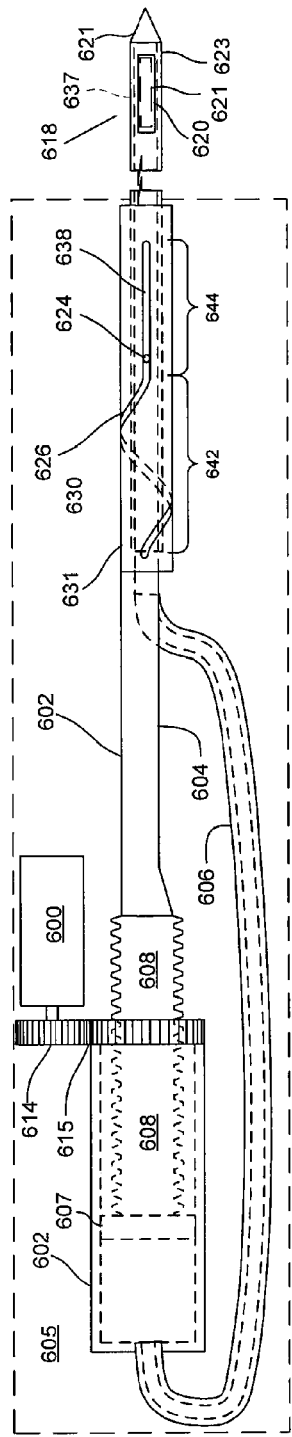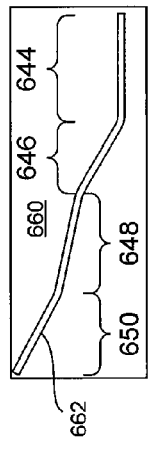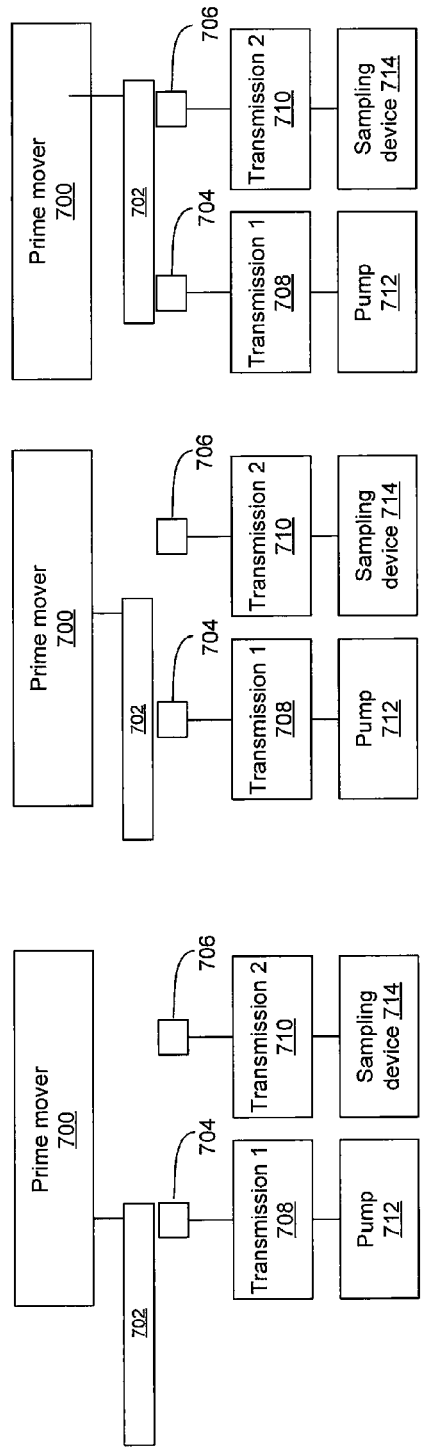

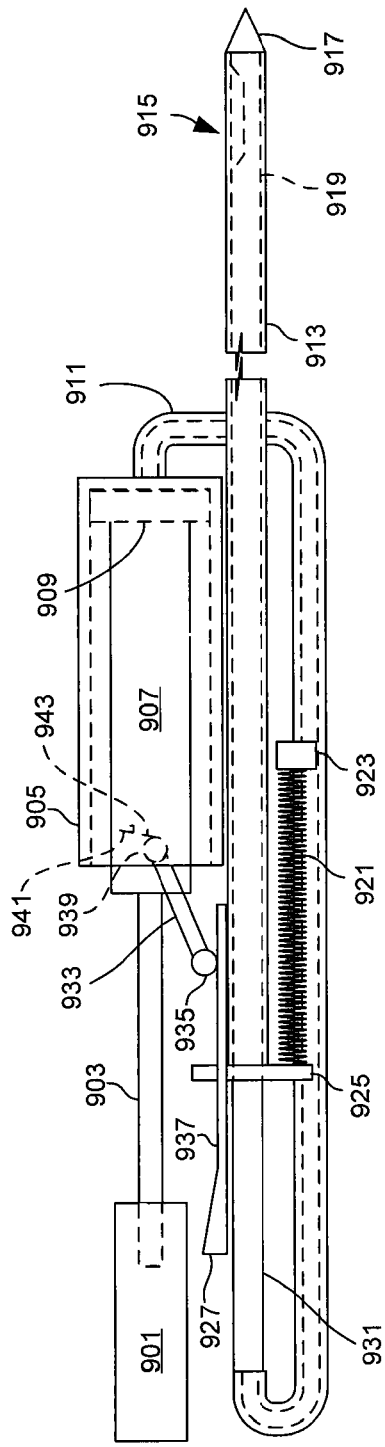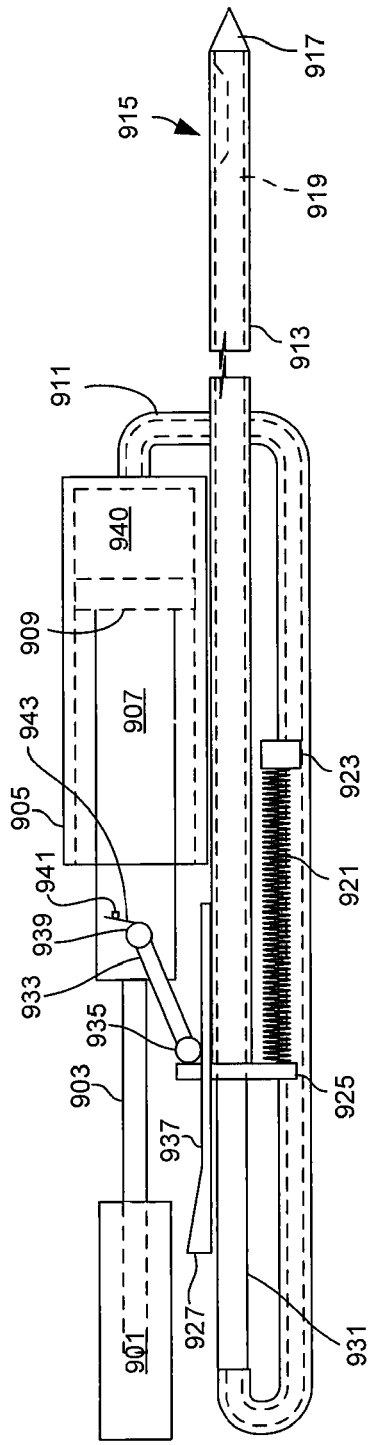
Fig. 12A
Fig. 12B

SELF-CONTAINED HANDHELD BIOPSY NEEDLE

PRIORITY DATA AND INCORPORATION BY REFERENCE

This application is a continuation of U.S. patent application Ser. No. 13/572,782 filed Aug. 13, 2012, now U.S. Pat. No. 8,951,208, which is a continuation of U.S. patent application Ser. No. 12/438,020 filed Feb. 19, 2009, now U.S. Pat. No. 8,251,917, which is a U.S. national phase of International Application No. PCT/US2007/076214, filed Aug. 17, 2007, which claims priority to U.S. Provisional Application Ser. No. 60/823,038, filed Aug. 21, 2006, each of which is hereby incorporated by reference in its entirety.

TECHNICAL FIELD

This invention relates to a tissue biopsy sampling device. More specifically, the invention relates to mechanical features of an automatic biopsy sampling device.

BACKGROUND

Often, it is either desirable or necessary to obtain specimens of tissue from humans and other animals, particularly in the diagnosis and treatment of patients with cancerous tumors, premalignant conditions, and other diseases or disorders. For example, when it is discovered that suspicious conditions exist, either by means of x-ray or ultrasound imaging in various tissues of the body, a physician typically performs a biopsy to determine if the cells at the suspected site are cancerous.

A biopsy can be done either by an open or percutaneous technique. Open biopsy is an invasive procedure using a scalpel, whereby either a portion (incisional biopsy) or the entire mass (excisional biopsy) is removed. Percutaneous biopsy is usually done with a needle-like instrument through a relatively small incision, and can be performed by fine needle aspiration (FNA) or through the taking of a core biopsy sample. In FNA biopsy, individual cells or clusters of cells are obtained for cytologic examination and can be prepared such as in a Papanicolaou smear. In a core biopsy, a core or fragment of the tissue is obtained for histologic examination.

Intact tissue from the organ, lesion, or tumor is preferred by medical personnel in order to arrive at a definitive diagnosis regarding the patient's condition. In most cases only part of the tissue in question needs to be sampled. The portions of tissue extracted must be indicative of the organ, lesion, or tumor as a whole. Often, multiple tissue samples from various locations of the mass being sampled may be taken.

The percutaneous biopsy procedure can be performed utilizing various techniques and devices. An example is a method and a device that employs a biopsy needle for cutting tissue sample as described in British Patent Publication No. GB 2018601A. In the described biopsy device, living tissue is sucked into a cutting region under vacuum. The vacuum is created in the needle by employing connecting lines to a vacuum generator situated outside of a hand piece that holds the cannula. The cutting of the sample is done using a cutting mechanism that moves axially over the cannula. After sampling, the needle is withdrawn from the host and the sample is flushed out from the tip of the needle. The vacuum established in the hollow needle is regulated externally from the hand-piece.

Another biopsy mechanism is described in European Patent Publication No. EP 0890 339 A1. A biopsy needle with a cutting mechanism is integrated into a hand piece. The needle is connected via connections lines to an external vacuum generator and controls. The cutting device is moveable axially in the hollow space of the biopsy needle. A rotary movement, combined with a manual lengthwise push causes the cutting device to sample the tissue from the host. The sample is transported in the hollow channel of the needle. A similar arrangement is also shown by U.S. Pat. No. 5,526,822. In these devices, the vacuum generation mechanisms and controls are costly and tend to be provided in permanent fixtures that are separate from the disposable components. A manual biopsy device is known from German Patent No. DE 40 41 614 C1. In this device, a partial vacuum source is provided by a piston and cylinder pump. A similar partial vacuum-assisted biopsy device can be found in International Publication No. WO 96/28097, which has a syringe plunger arrangement located inside a manual device to create partial vacuum.

A vacuum-assisted biopsy device is described in U.S. Patent Publication No. 2001/0011156 A1, provides for a compactly configured hand device, in whose housing all drive elements necessary for propelling the needle of the biopsy needle arrangement are provided. However, a partial vacuum source is provided separate from the hand device, which can be connected via an appropriate supply line to the needle arrangement inside the hand device at a suitable connection location.

US Patent No. 20050203439, hereby incorporated herein by reference in its entirety, describes a biopsy device for taking tissue samples, which includes a housing, a removable element and a control panel. The removable part has a vacuum pump in the form of a syringe which is driven by a first motor and a biopsy needle which is driven by a separate motor under the control of a controller built into a permanent hand set. The needle and syringe are provided as a sterile package unit.

There is a need for improvements in biopsy devices that provide for high performance with low manufacturing cost, simplicity, reliability, and ease of use. Current devices are complex, either requiring many parts such as motors and drive components or providing low performance such as weak low penetration force, small sample size, poor sample integrity, etc. There is a need for design features that permit a biopsy device to be fully automated, yet fully disposable as well as economical, susceptible to efficient manufacture, simple, and reliable.

DISCLOSURE OF THE INVENTION

The embodiments disclosed herein relate to self-contained hand-held biopsy needles with various features relating to automated sampling and recovery. Among the disclosed features are ones suited to fully-disposable single-use automatic biopsy devices, such as light weight, low cost, and simple design.

According to an embodiment, a biopsy device is provided which has a housing and a biopsy needle projecting from the housing. The biopsy needle has a first member that defines a sample chamber and a second member that defines a sample volume within the sample chamber. A pump generates a vacuum in the sample volume. A primary drive element has a first drive interval and a second drive interval. A first transmission is driven by the primary drive element during the first drive interval to operate the pump and a second transmission driven by the primary drive element during the second drive interval to position the first and second members of the biopsy needle to define the sample volume.

Preferably, a housing encloses the pump, the primary drive element, the first transmission, the second transmission, and a portion of the biopsy needle. The first and second drive intervals are sequential. The first drive interval overlaps the second drive interval. The second drive interval follows after the start of the first drive interval. The first and second drive intervals are physical displacement intervals. The first and second drive intervals have identical endpoints and the second drive interval begins after the beginning of the first drive interval. The device includes a motor with an output connected to the primary drive element and a controller selectively operates the motor in forward and reverse directions.

According to another embodiment a biopsy device is provided which has a biopsy needle with tissue-penetration and tissue-sampling configurations. A pump is connected to the biopsy needle to generate a vacuum in the biopsy needle. A first drive element is connected to operate the pump. A second drive element is provided to configure the biopsy needle. The first drive element has a first displacement interval and a second displacement interval such that during the first displacement interval, the first drive element operates the pump to generate a vacuum in the biopsy needle, and during the second displacement interval, the first drive element engages the second drive element to configure the biopsy needle into the tissue-sampling configuration.

Preferably, the second displacement interval follows the first displacement interval. Also, preferably, the first displacement interval overlaps the second displacement interval. Also, preferably, the second displacement interval follows after the start of the first displacement interval. The first and second displacement intervals can have the same endpoints and the second displacement interval preferably starts after the start of the first displacement interval. Preferably, a motor provides an output connected to the first drive element and a controller selectively operates the motor in forward and reverse directions. Also, preferably, a housing encloses the pump, the first and second drive elements, and a portion of the biopsy needle.

According to another embodiment a biopsy device is provided which has a biopsy needle selectively configurable into a sampling configuration for creating a tissue sample and an insertion/removal configuration for inserting or extracting the biopsy needle from living tissue. A pump connected to the biopsy needle generates a vacuum therein. A first drive element is provided which is connected to drive the pump. A second drive element is also connected to configure the biopsy needle. A primary drive member is displaced through a continuous range having a first interval and a second interval. During the first interval, a motive force is transmitted through the primary drive member to the first drive element to cause the pump to generate a vacuum and, during the second interval, a motive force is transmitted to the second drive element to configure the biopsy needle from the insertion/removal configuration to the sampling configuration. During the second interval, a motive force continues to be transmitted to the first drive element to cause the pump to continue generating a vacuum. Preferably, the continuous range has a third interval, following the second interval, during which the second drive element configures the biopsy needle from the sampling configuration to the insertion/withdrawal configuration. Also, preferably, the first drive element is spaced apart from the second drive element such that the primary drive member engages the first drive element during the first interval and, as it moves toward the second drive element, engages the second drive element during the second interval.

According to another embodiment a biopsy device is provided which has a biopsy needle selectively configurable into a cutting configuration, for cutting a tissue sample, and an insertion configuration, for insertion into a host. A pump is connected to the biopsy needle to generate a vacuum therein. A prime mover is provided with a primary output element, which can be displaced through first and second intervals. A transmission mechanism is connected to the primary output element. The transmission mechanism has at least a first transmission output to configure the biopsy needle and at least a second transmission output to operate the pump. The transmission mechanism is configured to cause the pump to generate a vacuum during a first displacement of the primary output element and to configure the biopsy needle from the insertion configuration to the cutting configuration during a second displacement of the primary output element. Preferably, the transmission mechanism includes a first drive element and a second drive element spaced apart therefrom. Also, preferably, the first and second drive elements drive the first and second transmission outputs, respectively. In this case, the primary output element is arranged to drive the first drive element during the first displacement and to move at least one of the first drive element and the primary drive element toward the second drive element until it engages and drives the second drive element and thereafter drive the second drive element during the second displacement.

According to another embodiment a biopsy device is provided which has a biopsy needle that is selectively configurable into a sampling configuration and an insertion configuration. The device has a pump connected to the biopsy needle to generate a vacuum therein. A motor and a transmission mechanism is provided where the transmission mechanism is configured to transmit motive force from the motor to the pump during a first interval upon activation of the motor, and, during a second interval, following the first interval, to transmit motive force from the motor to the biopsy needle to change its configuration from the insertion configuration to the sampling configuration such that a substantial vacuum is generated by the pump before the biopsy needle is configured into the sampling configuration. Preferably, the motor operates continuously during the first and second intervals. More preferably, both the pump and the motor operate continuously during the first and second intervals. In an embodiment, the pump is operates continuously during the first and second intervals.

The sampling configuration can include a continuous cycle that includes receiving a tissue sample within the biopsy needle and cutting the tissue sample from a host. The biopsy needle has fixed shaft, a longitudinal axis, and a rotating shaft movably connected to the fixed shaft to rotate around the longitudinal axis. The rotating shaft can include a cutting blade to cut tissue samples. The sampling configuration can also include a continuous sampling cycle, during the second interval, in which a tissue sample is cut and received within the biopsy needle, the transmission mechanism being configured to urge the rotating shaft progressively during the second interval to cut a tissue sample and cause it to be received in the biopsy needle.

According to another embodiment a biopsy device is provided which has a biopsy needle, selectively configurable into a sample access configuration and an insertion configuration. The biopsy needle has a sample chamber. The device also has a pump connected to the sample chamber to generate a vacuum therein and a motor with a transmission mechanism. The transmission mechanism is connected to configure the biopsy needle and drive the pump, upon activation of the motor in a first direction. The transmission mechanism transmits motive force from the motor to the pump during a first interval and, as the motor continues during a second interval that follows the first interval, the transmission mechanism transmits motive force to the biopsy needle to change its configuration from the insertion configuration to the sample access configuration such that a substantial vacuum is generated in the sample chamber before the biopsy needle is configured into the sample access configuration.

Preferably, upon activation of the motor in a second direction, the transmission mechanism transmits a motive force from the motor to the pump during a third interval following the second interval and simultaneously change the biopsy needle configuration from the insertion configuration to the sample access configuration to generate pressure in the sample chamber to eject a sample therefrom. The pump is preferably operated during at least part of the second interval. Preferably, the pump is operated throughout the second interval. Also, preferably, a housing encloses the pump, the transmission mechanism, and a portion of the biopsy needle.

According to another embodiment a biopsy device is provided which has a biopsy needle with an elongate inner cylindrical member and an elongate outer cylindrical member, the outer cylindrical member being coaxially aligned with the inner cylindrical member and rotatable with respect to it. The inner cylindrical member has a port and the outer cylindrical member has a cover portion capable of being aligned with the port to cover it for insertion of the biopsy needle. The outer cylindrical member has a cutting edge adjacent to the cover portion such that, as the outer cylindrical member is rotated progressively about the inner cylindrical member through a specified interval, the cutting edge passes over the port and covers the port. The cutting edge and port is shaped such may as the outer cylindrical member rotates, a progressively greater fraction of the cutting edge passes over the port.

Preferably, the inner cylindrical member has a trocar affixed to a distal tip thereof. Preferably, also, the cutting edge has at least a portion that is angled relative to the perpendicular to the direction of advance of the cutting edge. The inner cylindrical member has a surface with at least one barb aligned with a port edge of the port opposite the cutting edge as the cutting edge advances toward the port edge prior to covering the port. The inner cylindrical member can have a sharp edge partly defining the port, the sharp edge having a portion extending toward the axis of the inner cylindrical member and opposite the cutting edge as the cutting edge advances toward the port edge prior to covering the port.

According to another embodiment a biopsy device is provided which has a housing that defines a chamber with a biopsy needle partially disposed in the chamber. The biopsy needle has a first member that defines a sample chamber and a second member may define a sample volume with the sample chamber. The device has a pump that generates a vacuum at the sample chamber and a primary drive element positioned with the housing. The primary drive element has a first drive interval and a sequential second drive interval. A first transmission driven by the primary drive element during the first drive interval operates the pump. A second transmission driven by the primary drive element during the second drive interval positions the first and second members of the biopsy needle to define the sample volume.

According to another embodiment a biopsy device is provided which has a biopsy needle with a sample chamber that has an access opening. The biopsy needle has a cover member movable relative to the access opening to cover the access opening. A pump is connected to the biopsy needle to generate a vacuum in the sample chamber. A drive element is provided that simultaneously drives the pump and moves the cover member relative to the access opening through a sampling cycle over which the pump generates a vacuum in the sample chamber and the cover member moves relative to the sample chamber through a delay interval in which the access opening remains covered by the cover member and through a sampling interval, following the delay interval, in which the access opening is uncovered. The cover member has a cutting edge which cuts a sample free of a host after the access opening is uncovered.

According to another embodiment, a biopsy device includes an elongate inner cylindrical member and an elongate outer cylindrical member. The outer cylindrical member is coaxially aligned with the inner cylindrical member and movable with respect to it along a common axis of the inner and outer cylindrical members. The inner cylindrical member has a port and the outer cylindrical member has a cover portion capable of being aligned with the port to cover it for insertion of the biopsy needle. A drive mechanism drives a first transmission member connected to a vacuum pump. The first transmission member drives a second transmission member connected to the outer cylindrical member to displace it without rotating it. The outer cylindrical member has a cutting edge adjacent to the cover portion such that, as the outer cylindrical member is displaced along the inner cylindrical member by the drive mechanism, the cutting edge passes over the port and covers the port. Preferably, the vacuum pump is connected to the inner cylindrical member to create a vacuum in communication with the port. The inner cylindrical member would ordinarily have a cutting tip, such as a trocar affixed to a distal tip thereof.

BRIEF DESCRIPTION OF THE DRAWINGS

The accompanying drawings, which are incorporated herein and constitute part of this specification, illustrate presently preferred exemplary embodiments of the invention, and, together with the general description given above and the detailed description given below, serve to explain features of the invention.

FIG. 5A is a section view of a biopsy needle sample chamber with a tissue retention feature on an edge of the chamber.

FIG. 5B is a section view of a biopsy needle sample chamber with a tissue retention feature including barbs on an insert.

FIG. 6A is a graph of pressure and a timing diagram showing the operation of a vacuum pump and a biopsy needle.

FIGS. 6B to 6E are illustrations of a sequence of operation of a sampling needle.

FIGS. 7A to 7C are illustrations of the operation of a biopsy needle and drive mechanism in successive stages of an operating cycle.

FIG. 10A illustrates another embodiment of a biopsy needle and drive mechanism employing a cam mechanism.

FIG. 10B is a planar development of a variation on the cam drive mechanism of FIG. 8A.

FIGS. 12A to 12F show a biopsy needle embodiment for illustrating features including a linear actuator, an axial cutting sheath, and a spring-activated cutting action.

MODES FOR CARRYING OUT THE INVENTION

Figure 1A:
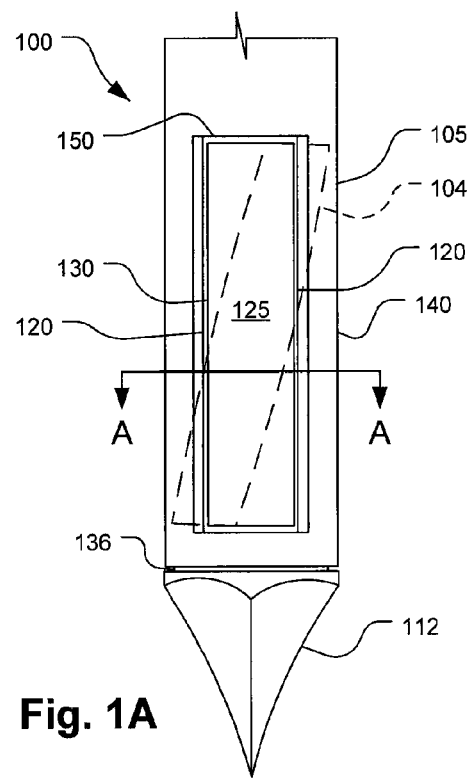
FIGS. 1A to 1F illustrate a biopsy needle with an external cutting sheath according to an embodiment.

FIGS. 1A to 1F illustrate a biopsy needle 100 with an outer sheath 105. Referring to FIG. 1A, the outer sheath 105, in the present embodiment, is cylindrical and has an opening 150 with at least one sharp edge defining a blade 120. A cylinder-shaped inner sheath 136 has a port 130, which, in FIG. 1A, is aligned with the opening 150. The port 130 provides access to a sample chamber 125 which is defined by a sample volume within the inner sheath 136. A trocar 112 is affixed to a distal end of the inner sheath 136. A handle (not shown) is presumed to be provided, opposite the trocar 112, to support the biopsy needle 100.

Figure 1B:
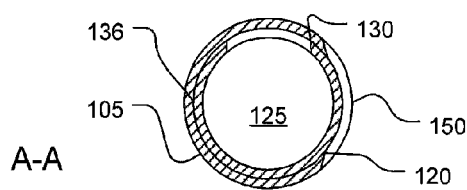

FIGS. 1B through 1F show, in section A-A, the needle 100 of FIG. 1A in successive stages of a sampling operation. These stages occur after the needle 100 is inserted into living tissue, a sample of which is to be excised for a biopsy. In FIG. 1B, the outer sheath 105 begins in a position in which it covers the port 130. The needle 100 is inserted while the outer sheath 105 is in this position relative to the inner sheath 136. Once the biopsy needle 100 is in position for sampling, the outer sheath 105 is rotated progressively in a counter-clockwise direction. The counter-clockwise rotation of the outer sheath 105 proceeds progressively through the stages indicated by FIGS. 10 through 1F. The outer sheath 105 may be driven by any suitable drive mechanism including pneumatic, electrical, magnetic, hydraulic, etc. Embodiments of suitable drive mechanisms are discussed below.

While the biopsy needle is in the insertion position shown in FIG. 1B, and after insertion into the tissue to be sampled (not shown), a vacuum is generated in the sample chamber 125 by withdrawing air from the inner sheath 136. The vacuum may be generated by any suitable device. Embodiments of suitable vacuum mechanisms are discussed below. Once a vacuum has been generated, the outer sheath 105 begins to rotate in the counter-clockwise direction. In FIG. 10, the opening 150 is shown after having moved partly toward a position of coincidence with the port 130. As the rotation proceeds, the blade 120 advances toward the port 130. In this position, the vacuum, created in the sample chamber 125, draws tissue to be sampled through the opening 150 and port 130 until it begins to enter the sample chamber 125. The outer sheath 105, at this point, moves counter-clockwise toward the position shown in FIG. 1D where the port 130 is fully uncovered, the opening 150 having moved into coincidence with the opening 130. The vacuum causes tissue to be drawn into the sample chamber 125 and the outer sheath 105 continues rotating in the counter-clockwise direction to the position shown in FIG. 1E.

Figure 1D:
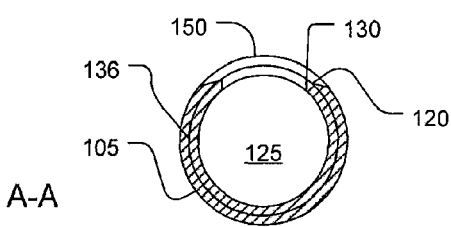
Figure 1E:
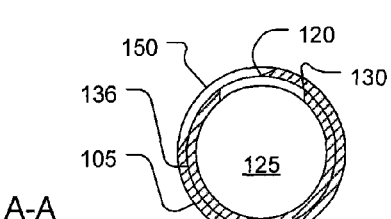

As the outer sheath 105 rotates toward the position shown in FIG. 1E, the blade 120 partly slices the tissue that has been drawn into the sample chamber 125. As the blade 120 continues toward the position of FIG. 1F, the tissue sample is completely severed from the host and held within the sample chamber 125 while a portion of the outer sheath 105, behind the blade 120, covers the port 130. The biopsy needle 100 can then be withdrawn from the inserted position as it retains the sample. Note that the present cutting mechanism, as well as others disclosed in the present application, may be replaced by suitable alternative cutting devices such as levered or rotating knives with blades of varying shape, radio-frequency (RF) cutting tools, laser cutters, or any other suitable cutting device.

To remove the tissue sample, the operation depicted in FIGS. 1B through 1F may be repeated. However, in this case, a positive pressure may be generated in sample chamber 125 before starting the cycle. As the outer sheath 105 rotates clockwise through the successive positions starting with the one shown in FIG. 1F, a pressure is applied to the sample chamber 125 and the port 130 is uncovered. This causes the pressure in sample chamber 125 to force the tissue sample out through the uncovered port (about the position shown in FIG. 1D). The cycle may then continue to the point shown in FIG. 1B. Note that other sample-removal mechanisms may also be employed, such as a mechanical member pushing the sample from the sample chamber 125, a fluid wash. Alternatively, a sample chamber liner, such as of thermoformed polymer, may be preinstalled and removed by hand.

Note that the outer sheath 105 could rotate in either direction, or both directions, in alternative embodiments. For example, the port 130 could be uncovered by rotating in one direction and the cutting operation and covering could occur after reversing the direction of rotation immediately after uncovering the port 130. This alternative may be provided for all of the embodiments described herein. In addition, the blade 120 may be on either or both sides of the opening 150.

The speed of rotation of the outer sheath 105 may be constant or variable. For example, to reduce or amplify torque from the drive mechanism, a reduced force/torque transmission ratio of the drive may be provided to level the prime mover load through the cutting phase.

Referring again to FIG. 1A, an alternative shape for the port 130 is indicated in FIG. 1A at 104. This alternative port 104 may also be used to help reduce the instantaneous torque load on the outer sheath 105 drive mechanism (not shown). The shape of the port 130, as may be confirmed by inspection, is such that the blade 120 advances through only a fraction of the longitudinal extent of the sample at a given instant of time.

Figure 2A:
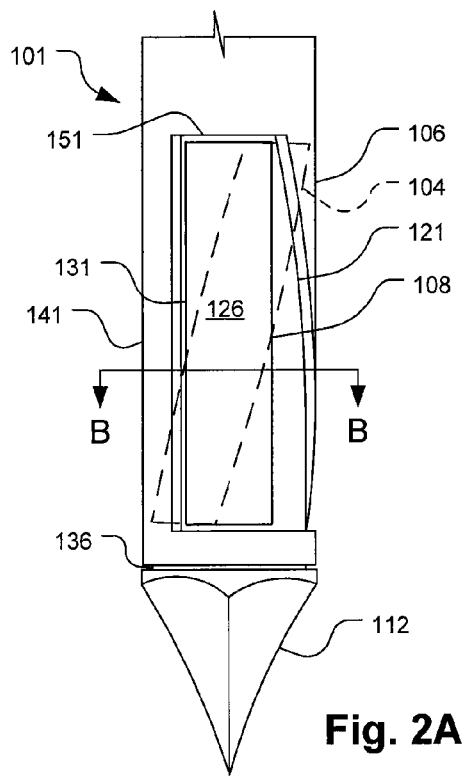
FIGS. 2A to 2F illustrate a biopsy needle with an external cutting sheath according to another embodiment.

The embodiment of FIGS. 2A through 2F is similar to the embodiment of FIGS. 1A through 1F except that an angled blade 121 is provided to level the cutting load. FIGS. 2A to 2F illustrate a biopsy needle 101 with an outer sheath 106. Referring to FIG. 2A, the outer sheath 106, in the present embodiment, is cylindrical and has an opening 151 with at least one sharp edge defining an angled blade 121. A cylinder-shaped inner sheath 136 has a port 131, which, in FIG. 2A, is aligned with the opening 151. The port 131 provides access to a sample chamber 126 which is defined by a volume within the inner sheath 136. As in the previous embodiment, a trocar 112 is affixed to a distal end of the inner sheath 136 and a handle (not shown) is presumed to be affixed, opposite the trocar 112, to support the biopsy needle 101. Again, it should be clear that other cutting mechanisms may be employed and the mechanical details of the disclosed embodiments can be modified while still providing the functionality disclosed.

As mentioned, the embodiment of FIGS. 2A through 2F is similar in structure and operation to the embodiment of FIGS. 1A through 1F with a cutting blade 121 that forms a non-zero angle with the longitudinal axis of the outer sheath 106. This angled shape may help reduce the instantaneous torque load on the outer sheath 105 drive mechanism (not shown). The shape of the port 131, as may be confirmed by inspection, is such that the blade 121 advances through only a fraction of the longitudinal extent of the sample at a given instant of time. Because the blade 121 is angled, it defines a helical contour with the outer sheath 106. In alternative embodiments, the blade 121 could have a curved or multiple-angle configuration to achieve the same function of reducing the instantaneous force required to perform cutting.

Figure 2B:
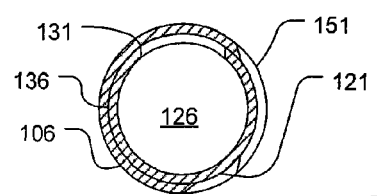
Figure 1C:
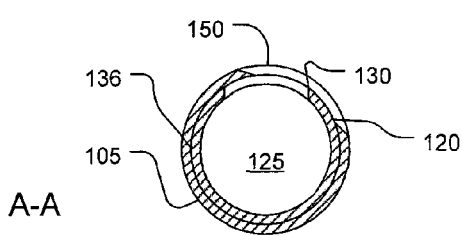

FIGS. 2B through 2F show, in section B-B, the needle 100 of FIG. 2A in successive stages of a sampling operation. These stages occur after the needle 101 is inserted into living tissue to sample the tissue of a host. In FIG. 2B, the outer sheath 106 begins in a position in which it covers the port 130. The needle 100 is inserted while the outer sheath 106 is in this position relative to the inner sheath 136. Once the biopsy needle 101 is in position for sampling, the outer sheath 106 is rotated progressively in a counter-clockwise direction. The counter-clockwise rotation of the outer sheath 106 proceeds progressively through the stages indicated by FIGS. 2C through 2F. The outer sheath 106 may be driven by any suitable drive mechanism. Embodiments of suitable drive mechanisms are discussed below.

Figure 2C:
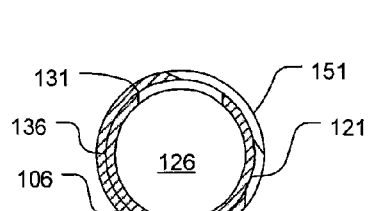
Figure 2D:
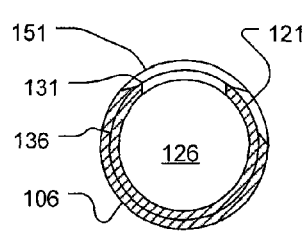

While the biopsy needle is in the insertion position shown in FIG. 2B, and after insertion into the tissue to be sampled (not shown), a vacuum is generated in the sample chamber 126 by drawing air through the inner sheath 136. The vacuum may be generated by any suitable device. Embodiments of suitable vacuum mechanisms are discussed below. Once a vacuum has been generated, the outer sheath 106 begins to rotate in the counter-clockwise direction. In FIG. 2C, the opening 151 is shown after having moved partly toward a position of coincidence with the port 131. As the rotation proceeds, the blade 121 advances toward the port 131. In this position, the vacuum, created in the sample chamber 126, draws tissue to be sampled through the opening 151 and port 131 until it begins to enter the sample chamber 126. The outer sheath 106, at this point, moves counter-clockwise toward the position shown in FIG. 2D where the port 131 is fully uncovered, the opening 151 having moved into coincidence with the opening 131. The vacuum causes tissue to be drawn into the sample chamber 126 and the outer sheath 106 continues rotating in the counter-clockwise direction to the position shown in FIG. 2E.

Figure 2E:
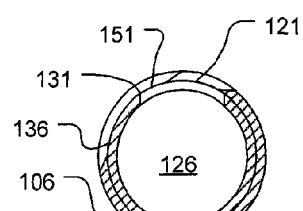
Figure 1F:
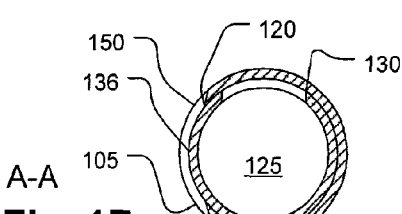
Figure 2F:
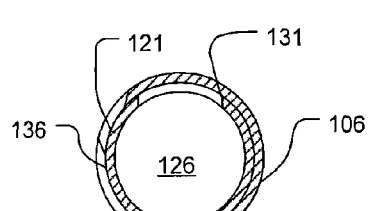

As the outer sheath 106 rotates toward the position shown in FIG. 2E, the blade 121 partly slices the tissue that has been drawn into the sample chamber 126. As the blade 121 continues toward the position of FIG. 2F, the tissue sample is completely severed from the host and held within the sample chamber 126 while a portion of the outer sheath 106 behind the blade 121 covers the port 131. The biopsy needle 101 can then be withdrawn from the inserted position as it retains the sample.

To remove the tissue sample, the operation depicted in FIGS. 2B through 2F may be repeated. However, in this case, a positive pressure may be generated in sample chamber 126 before starting the cycle. As the outer sheath 106 rotates clockwise through the successive positions starting with the one shown in FIG. 2F, a pressure is applied to the sample chamber 126 and the port 131 is uncovered. This causes the pressure in sample chamber 126 to force the tissue sample out through the uncovered port (about the position shown in FIG. 2D). The cycle may then continue to the point shown in FIG. 2B.

Note that the outer sheath 106 could rotate in either direction with an appropriate repositioning of the blade 121. In addition, the blade 121 may be on both sides of the opening 151. As in the prior embodiment, the speed of rotation of the outer sheath 106 may be constant or variable to amplify torque from the drive mechanism. Referring again to FIG. 2A, the alternative shape for the port 131 indicated in FIG. 2A at 104 is substantially as discussed with reference to FIG. 1A. However, this alternative port 104 may provide even lower instantaneous torque load for a given angle because the angle of the cutting blade 121 causes the cutting front to be even smaller for a given angle of the port 131.

The movement of the outer sheath 105 or 106 of the foregoing embodiments may be permitted by providing that the inner sheath 135 or 136 be journaled within the outer sheath 105 or 106. A lubricant may or may not be provided.

Referring back to FIGS. 1A and 1B, the opening 150 may be made narrow enough, in a circumferential direction, such that the port 130 is barely uncovered before severing of a tissue sample begins. However, it may be desirable to provide a wider opening 150 to provide more time for tissue to be drawn into the sample chamber 125. There is a tradeoff against structural strength in making the opening 150 wider. However, in alternative embodiments, the opening 150 may be made wider in a circumferential direction and in the extreme, only enough of the outer sheath 105 may remain to barely cover the port 130. Such an embodiment is shown in FIGS. 3A to 3F and described immediately below.

Figure 3A:
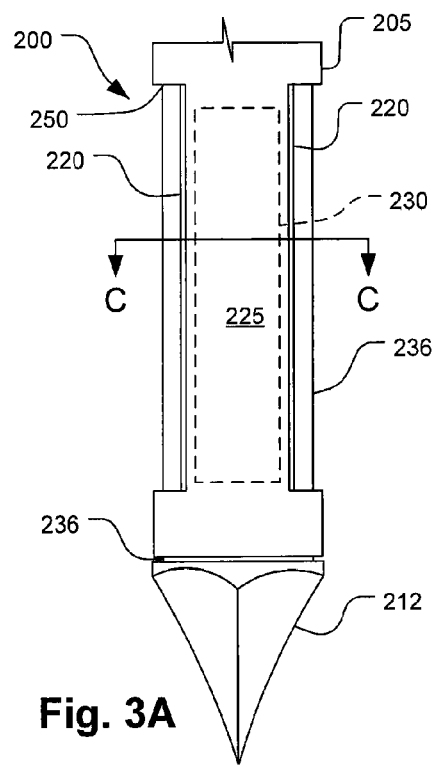
FIGS. 3A to 3F illustrate a biopsy needle with an external cutting sheath according to a yet another embodiment.

FIGS. 3A to 3F illustrate a biopsy needle 200 with an outer sheath 205. Referring to FIG. 3A, the outer sheath 205, in the present embodiment, is cylindrical and has an opening 250 with at least one sharp edge defining a blade 220. A cylinder-shaped inner sheath 236 has a port 230, which, in FIG. 3A, is aligned with the opening 250. The port 230 provides access to a sample chamber 225 which is defined by a volume within the inner sheath 236. A trocar 212 is affixed to a distal end of the inner sheath 236. A handle (not shown) is presumed to be provided, opposite the trocar 212, to support the biopsy needle 201.

Figure 3B:
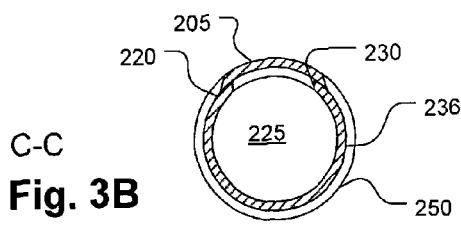

FIGS. 3B through 3F show, in section C-C, the needle 200 of FIG. 3A in successive stages of a sampling operation. These stages occur after the needle 200 is inserted into living tissue, a sample of which is to be excised for a biopsy. In FIG. 3B, the outer sheath 205 begins in a position in which it covers the port 230. The needle 200 is inserted while the outer sheath 205 is in this position relative to the inner sheath 236. Once the biopsy needle 200 is in position for sampling, the outer sheath 205 is rotated progressively in a counter-clockwise direction. The counter-clockwise rotation of the outer sheath 205 proceeds progressively through the stages indicated by FIGS. 3C through 3F. The outer sheath 205 may be driven by any suitable drive mechanism. Embodiments of suitable drive mechanisms are discussed below.

Figure 3C:
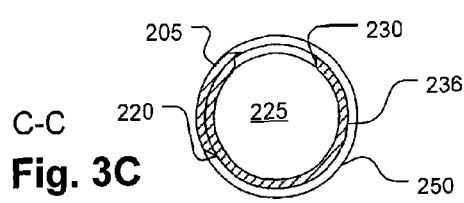

While the biopsy needle is in the insertion position shown in FIG. 3B, and after insertion into the tissue to be sampled (not shown), a vacuum is generated in the sample chamber 225 by drawing air through the inner sheath 236. The vacuum may be generated by any suitable device. Embodiments of suitable vacuum mechanisms are discussed below. Once a vacuum has been generated, the outer sheath 205 begins to rotate in the counter-clockwise direction. In FIG. 3C, the opening 250 is shown after having moved partly toward a position of coincidence with the port 230. As the rotation proceeds, the blade 220 advances toward the port 230. In this position, the vacuum, created in the sample chamber 225, draws tissue to be sampled through the opening 250 and port 230 until it begins to enter the sample chamber 225. The outer sheath 205, at this point, moves counter-clockwise toward the position shown in FIG. 3D where the port 230 is fully uncovered, the opening 250 having moved into coincidence with the opening 230. The vacuum causes tissue to be drawn into the sample chamber 225 and the outer sheath 205 continues rotating in the counter-clockwise direction to the position shown in FIG. 3E.

Figure 3D:
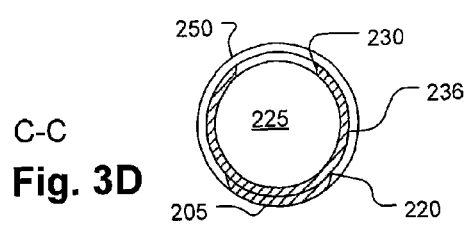
Figure 3E:
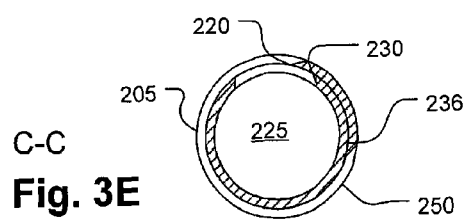

As the outer sheath 205 rotates toward the position shown in FIG. 3E, the blade 220 partly slices the tissue that has been drawn into the sample chamber 225. As the blade 220 continues toward the position of FIG. 3F, the tissue sample is completely severed from the host and held within the sample chamber 225 while a portion of the outer sheath 205 behind the blade 220 covers the port 230. The biopsy needle 200 can then be withdrawn from the inserted position as it retains the sample.

To remove the tissue sample, the operation depicted in FIGS. 3B through 3F may be repeated. However, in this case, a positive pressure may be generated in sample chamber 225 before starting the cycle. As the outer sheath 205 rotates clockwise through the successive positions starting with the one shown in FIG. 3F, a pressure is applied to the sample chamber 225 and the port 230 is uncovered. This causes the pressure in sample chamber 225 to force the tissue sample out through the uncovered port (about the position shown in FIG. 3D). The cycle may then continue to the point shown in FIG. 3B.

As in the previous embodiments, the outer sheath 205 could rotate in either direction, or both directions, in alternative embodiments. For example, the port 130 could be uncovered by rotating in one direction and the cutting operation and covering could occur after reversing the direction of rotation immediately after uncovering the port 130. This alternative may be provided for all of the embodiments described herein. In addition, the blade 220 may be on either or both sides of the opening 250. As in the previous embodiments, the speed of rotation of the outer sheath 205 may be constant or variable. For example, to reduce amplify torque from the drive mechanism, a reduced force/torque transmission ratio of the drive may be provided to level the prime mover load through the cutting phase. As in the prior embodiments, the port 130 may have angled edges (as has port 104 in the embodiment of FIG. 1A) to help reduce the instantaneous torque load on the outer sheath 205 drive mechanism (not shown).

The embodiment of FIGS. 4A through 4F is similar to the embodiment of FIGS. 3A through 3F except that an angled blade 221 is provided to level the cutting load, as described with reference to the embodiment of FIGS. 2A through 2F.

Figure 4A:
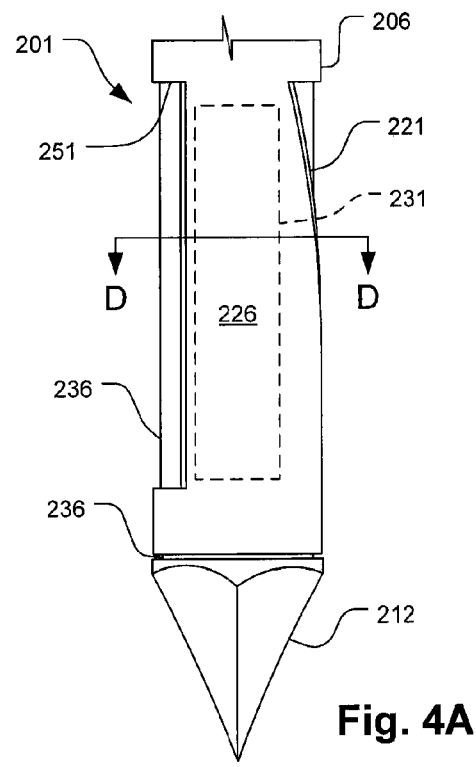
FIGS. 4A to 4F illustrate a biopsy needle with an external cutting sheath according to another embodiment.

FIGS. 4A to 4F illustrate a biopsy needle 201 with an outer sheath 206. Referring to FIG. 4A, the outer sheath 206, in the present embodiment, is cylindrical and has an opening 251 with at least one sharp edge defining a blade 221. A cylinder-shaped inner sheath 236 has a port 231, which, in FIG. 4A, is aligned with the opening 251. The port 231 provides access to a sample chamber 226 which is defined by a volume within the inner sheath 236. A trocar 212 is affixed to a distal end of the inner sheath 236. A handle (not shown) is presumed to be provided, opposite the trocar 212, to support the biopsy needle 200.

Figure 4B:
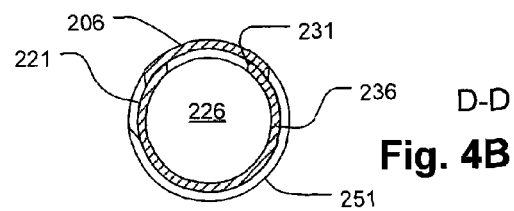

FIGS. 4B through 4F show, in section D-D, the needle 201 of FIG. 4A in successive stages of a sampling operation. These stages occur after the needle 201 is inserted into living tissue, a sample of which is to be excised for a biopsy. In FIG. 4B, the outer sheath 206 begins in a position in which it covers the port 231. The needle 201 is inserted while the outer sheath 206 is in this position relative to the inner sheath 236. Once the biopsy needle 201 is in position for sampling, the outer sheath 206 is rotated progressively in a counter-clockwise direction. The counter-clockwise rotation of the outer sheath 206 proceeds progressively through the stages indicated by FIGS. 4C through 4F. The outer sheath 206 may be driven by any suitable drive mechanism. Embodiments of suitable drive mechanisms are discussed below.

Figure 4C:
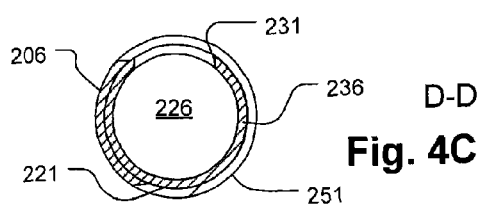
Figure 4D:
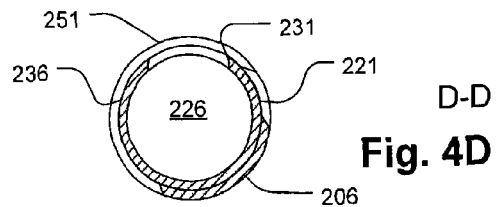

While the biopsy needle is in the insertion position shown in FIG. 4B, and after insertion into the tissue to be sampled (not shown), a vacuum is generated in the sample chamber 226 by drawing air through the inner sheath 236. The vacuum may be generated by any suitable device. Embodiments of suitable vacuum mechanisms are discussed below. Once a vacuum has been generated, the outer sheath 206 begins to rotate in the counter-clockwise direction. In FIG. 4C, the opening 251 is shown after having moved partly toward a position of coincidence with the port 231. As the rotation proceeds, the blade 221 advances toward the port 231. In this position, the vacuum, created in the sample chamber 226, draws tissue to be sampled through the opening 251 and port 231 until it begins to enter the sample chamber 226. The outer sheath 206, at this point, moves counter-clockwise toward the position shown in FIG. 4D where the port 231 is fully uncovered, the opening 251 having moved into coincidence with the opening 231. The vacuum causes tissue to be drawn into the sample chamber 226 and the outer sheath 206 continues rotating in the counter-clockwise direction to the position shown in FIG. 4E.

Figure 4E:
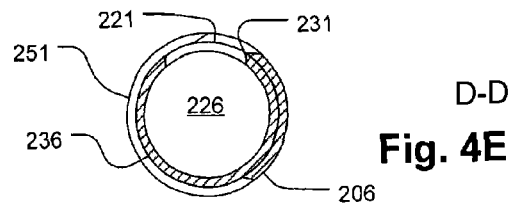
Figure 3F:
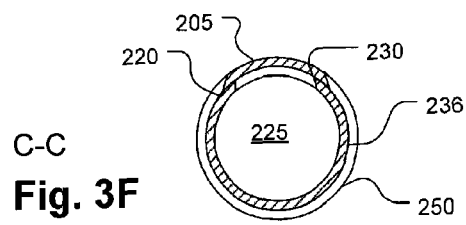
Figure 4F:
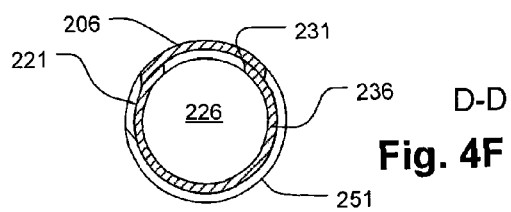

As the outer sheath 206 rotates toward the position shown in FIG. 4E, the blade 221 partly slices the tissue that has been drawn into the sample chamber 226. As the blade 221 continues toward the position of FIG. 4F, the tissue sample is completely severed from the host and held within the sample chamber 226 while a portion of the outer sheath 206 behind the blade 221 covers the port 231. The biopsy needle 201 can then be withdrawn from the inserted position as it retains the sample.

To remove the tissue sample, the operation depicted in FIGS. 4B through 4F may be repeated. However, in this case, a positive pressure may be generated in sample chamber 226 before starting the cycle. As the outer sheath 206 rotates clockwise through the successive positions starting with the one shown in FIG. 4F, a pressure is applied to the sample chamber 226 and the port 231 is uncovered. This causes the pressure in sample chamber 226 to force the tissue sample out through the uncovered port (about the position shown in FIG. 4D). The cycle may then continue to the point shown in FIG. 4B.

As in the previous embodiments, the outer sheath 206 could rotate in either direction, or both directions, in alternative embodiments. For example, the port 231 could be uncovered by rotating in one direction and the cutting operation and covering could occur after reversing the direction of rotation immediately after uncovering the port 231. This alternative may be provided for all of the embodiments described herein. In addition, the blade 221 may be on either or both sides of the opening 251. As in the previous embodiments, the speed of rotation of the outer sheath 206 may be constant or variable. For example, to reduce amplify torque from the drive mechanism, a reduced force/torque transmission ratio of the drive may be provided to level the prime mover load through the cutting phase. As in the prior embodiments, the port 231 may be angled (as is 104 relative to 130 in FIG. 1A) to help reduce the instantaneous torque load on the outer sheath 206 drive mechanism (not shown).

FIG. 5A is a section view of a biopsy needle 300 sample chamber 315 with a sharpened, curved, or jagged edge of a chamber opening 309. The edge 302 helps to keep a tissue sample drawn into the sample chamber 315 by a vacuum, from retreating during the cutting operation. The configuration of the biopsy needle 300 may be similar to the configurations of any of the foregoing embodiments but the configuration shown is similar to that of FIGS. 3A to 3F. As an outer sheath 306 rotates around an inner sheath 304, the cutting blade 310 advances across the opening 309 while the edge 302 helps to ensure the tissue does not retreat. Because the cutting blade 310 is on the outside sheath 306, an inwardly-directed edge treatment, represented as edge 302, may be provided without interfering with the operation of the cutting blade 310 or outer sheath 306.

The embodiment of FIG. 5B is similar to that of FIG. 5A except that the biopsy needle 301 configuration is closest to that of FIGS. 1A to 1F, although any of the foregoing configurations may be employed. Instead of an edge 302 as in the embodiment of FIG. 5A, the embodiment of FIG. 5B has an insert 328 which fits inside the sample chamber 316. The insert has a portion 321 with a barbed surface 320 that is opposite the cutting blade 332. As in the previous embodiment, as an outer sheath 330 rotates around an inner sheath 334, the cutting blade 332 advances across the opening 329 while the barbed surface 320 helps to ensure the tissue does not retreat. Because the cutting blade 332 is on the outer sheath 330, inwardly-directed barbs may be provided without interfering with the operation of the cutting blade 332 or outer sheath 330.

In the foregoing embodiments, it is preferable for a substantial vacuum to be generated before the biopsy needle is actuated for cutting. This is so that a poor sample specimen does not result due to the cutting operation getting underway before the tissue sample is drawn well into the sample chamber. This can be ensured in a variety of ways, for example by providing a drive system with independently controlled vacuum source and biopsy needle that are sequenced to generate the vacuum before the biopsy needle is placed into a configuration for sampling. FIG. 6A illustrates various sequencing operations and will be used to discuss the sequencing and variations of it.

Referring now to FIG. 6A, a self-contained device such as described hereinbelow or, for example, in US Patent Application No. 20050203439, incorporated by reference above, or any other vacuum source, may take a finite period of time to generate a terminal negative pressure. For example, a displacement pump that increases a contained volume, at a linear rate, produces a vacuum—assuming there are no leaks—characterized by an exponential pressure curve as indicated at 408. Similarly, such a pump operated in reverse generates a pressure according to an inclining exponential positive pressure curve as indicated at 410.

The vacuum is preferably established when the sample chamber is uncovered. This may ensure that the severing operation can be completed and the sample secured without the sample chamber being open for a long interval. In principle this is not essential, but in practice it may be desirable for various reasons: (1) an imperfect fluid seal may exist so that a progressive vacuum may not reach a desired peak level; (2) excess fluid may be drawn from the host, thereby compromising the vacuum and producing an undesirable result when a solid specimen is required; and (3) excessive fluid may be accumulated in the tissue sample due to an extended exposure to the vacuum, while attached to the host. Other effects such as compliance in the biopsy device's fluid circuit and other factors may also favor an operating sequence in which the host is exposed to the vacuum as briefly as possible. In all of the disclosed embodiments, means of anchoring tissue samples other than vacuum may be employed. For example, external pressure on the host tissue from outside the patient body (e.g. by means of a tissue compression device or manual pressure by the practitioner) may be employed alone, or in addition to vacuum, for forcing samples into the sample chamber.

The time during which a vacuum pump is operated to create the pressure curve, shown at 408, is indicated by the bar 402. For the entire period $t_0$ to $t_5$, a vacuum pump may be operated. At a point after a substantial vacuum is generated, for example $t_2$, the sample opening (e.g., as port 130 in FIG. 1A) may be opened 422. After the sample chamber is opened 424, the tissue sample, having been drawn in, will be cut 420 at a later time $t_3$ and the opening subsequently closed 424 during interval $t_4$ to $t_5$. In this way the opening and cutting operations are performed toward the end of the vacuum generation cycle 402 which takes place over the interval from $t_0$ to $t_5$, although it may be paused earlier, depending on the various factors mentioned.

The above sequencing may be achieved by employing independent drive mechanisms for the vacuum and biopsy needle. In a design suitable for a disposable biopsy needle it may be preferred to have a single drive system that can achieve the same operation sequence as just described in a manner that is reliable, with a simple a structure and low cost, by employing a single mechanical drive, as discussed below.

An embodiment of a biopsy needle 448, similar to the embodiment of FIGS. 1A and 1B, is illustrated by FIGS. 6B through 6E. In this embodiment, the outer sheath 105 (FIG. 1A) corresponds to the outer sheath 450, which has an opening 452. The inner sheath 130 (FIG. 1A) corresponds to the inner sheath 456 which has an opening 454. Either of the outer sheath 450 or the inner sheath 456 can have a cutting edge (for example at 451 on outer sheath 450) to cut a tissue sample, as discussed above, which is drawn into a sample chamber 458 by a vacuum generated therein. The present embodiment operates in a manner that is similar to what is described with reference to FIGS. 1B through 1F, except that the total angular displacement of the outer sheath 450 is greater in the present embodiment, to generate a delay from the onset of the operation of the vacuum generating device and the opening of the sampling device, as will be explained, presently.

In the series of figures, FIGS. 6B through 6E, a positive-displacement pump is shown at 480. In the series of figures, the outer sheath 450 is progressively rotated counter-clockwise as a piston 472 of the pump 480 is progressively displaced from the initial position indicated at 485, to create a vacuum in a line 474 connected to the sample chamber 458. As the outer sheath 450 is rotated from the insertion position shown in FIG. 6B to the position shown in FIG. 6C, the piston 472 is displaced, progressively as shown to draw a negative pressure in the line 474. As the outer sheath 450 is rotated further through the positions of FIGS. 6D and 6E, the piston 472 is displaced further until the sample chamber 458 is exposed and a sample is drawn into the sample chamber 458 and separated from the host. The final state is indicated at FIG. 6B with the pump 480 in the position indicated at 486, rather than the initial position indicated at FIG. 485.

It will be observed that the above operation of the needle 448 and pump 480 is effective to provide the sequencing of the vacuum creation and sampling cycle described above with reference to FIG. 6A. That is, the sample chamber 458 remains closed as the pump 480 is continuously operated to create a vacuum until the sample chamber 458 is opened at the final phase of vacuum generation. Referring particularly to FIG. 6B, it will also be observed that the outer sheath and the vacuum source are both operated continuously during the entire cycle so that a single drive 481 can move both the outer sheath 450 and the pump piston 472 continuously without any additional provisions for sequencing because a delay can be incorporated in the arrangement and configuration of the inner 456 and outer 450 sheaths. Referring particularly to FIG. 6C, a single drive 483 may also drive the pump 480 which in turn may drive the outer sheath 450 through a drive element 485 or the drive element 485 may be a single drive element that drives both the pump 480 and the outer sheath 450. Thus, a transmission configured to apply motive force, simultaneously, to rotate the sheath and to drive the vacuum source, will provide the desired operational sequence.

Referring again to FIG. 6A, a sample may be removed from a biopsy device by releasing pressurized air into the sample chamber 458 to eject the sample. A device may have a positive displacement pump that generates the pressure 406 gradually during an operating cycle, for example extending from a time t6 to a time t10 after the sample is taken. A positive pressure may be generated after the sample is retained in the sample chamber 458, as indicated by the curve 410. In this case, it may be desirable for a significant initial pressure to exist before the sample chamber 458 is opened 426 to release the sample. The desired point, during the operating cycle 406 of the pump, at which the sample chamber 458 is opened may vary, e.g., 426 or 428, based on the arrangement of the biopsy device and designer preference.

The mechanism of FIGS. 6B to 6E may be employed to provide a delay between the operation of the pump and the point at which the sample chamber 458 is opened. For example, if the pump 490 is operated in reverse, and the outer sheath 450 is rotated counter-clockwise, a pressure will accrue in the pump 480, while the sample chamber 458 remains closed until near the end of the pump cycle. The point at which the sample chamber 458 opens can be selected by selecting the initial position of the outer sheath 450 opening 452 relative to the inner sheath 456 opening 454.

Depending on the desired timing, both the pump 480 and the outer sheath may be moved in a reverse direction during the sample-ejection cycle, which may allow a simpler driving system. For example, if the initial and final positions of the outer sheath 450 are as shown in FIG. 6C, the opening of the sample chamber will occur in the middle of the pumping cycle in both the sampling and sample-ejection operations. In that case, the entire drive system may simply be reversed to obtain a sampling sequence in which the sample chamber opening is delayed relative to both the start of the vacuum cycle 402 during sampling and the start of the pressure-generating cycle 406 during sample-ejection. Also, the total angular displacement need not be 360° as illustrated above.

Referring now to FIGS. 7A to 7B, a sampling sequence may be delayed after initial operation of a pump without requiring independent drive systems for the pump and sampling device by another means. A prime mover 700 has an output represented by the bar 702 which translates to the right (as shown in the sequence of FIGS. 7A, 7B, and 7C) which indicates the displacement of the output 702. This is an illustration of the output 702, which could correspond to the shaft of a rotary motor, a linear actuator, a worm drive, or any kind of drive device. A first transmission 708 receives motive force from a drive input 704 and applies an output to a pump 712. A second transmission 710 receives motive force from a drive input 706 and applies an output to a sampling device 714. As the prime mover output 702 advances it first engages the first transmission input 704 as shown in FIG. 7A causing the pump to begin an operating cycle. As it progresses, the prime mover output 702 continues to advance to the point shown in FIG. 7B and as it advances, it continues to remain in engagement with the first transmission input 704, but has not yet reached the second transmission input 706. Eventually, the prime mover output 702 advances to the point shown in FIG. 7C and, as it advances, it engages and continues to remain in engagement with the first transmission input 704 and the second transmission input 706 to drive both the pump 712 and the sampling device 714.

In the foregoing mechanism, it is possible to allow the pump 712 to disengage from the prime mover output 702 at a desired point in the cycle. This may be desirable to level the load on the prime mover 700 so that it does not require the capacity to operate the pump 712 and the sampling device 714, simultaneously.

Figure 8A:
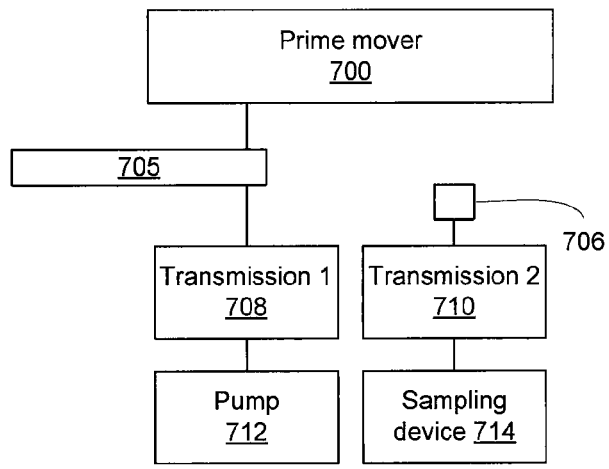
FIGS. 8A to 8C are illustrations of the operation of a biopsy needle and drive mechanism in successive stages of an operating cycle according to a further embodiment.
Figure 8B:
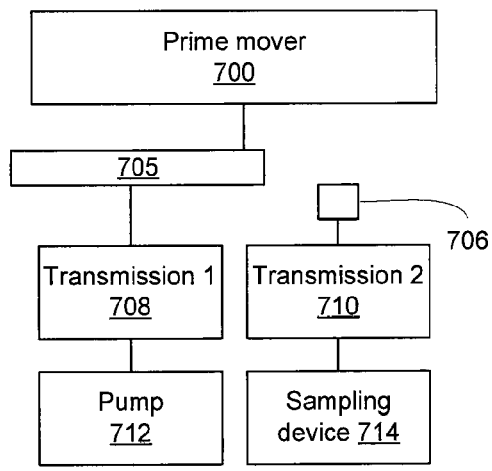
Figure 8C:
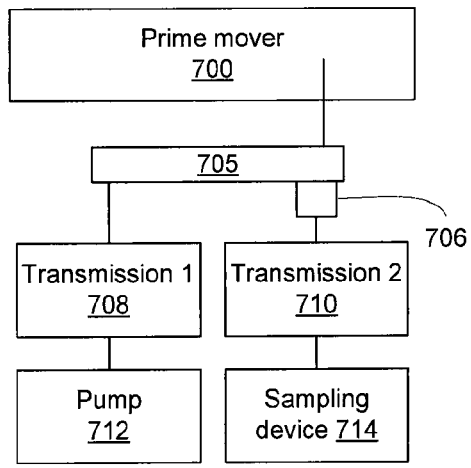

Referring now to FIGS. 8A to 8C, another mechanism to provide the sequencing of a pump 712 and sampling device 714, in a similar manner to that of FIGS. 7A to 7C is to connect the prime mover directly to a combined first transmission input and prime mover output 705. This combined first transmission input applies motive force to the pump 712 and, as it translates to the right, continues to operate the pump 712 until, as indicated in FIG. 8C, it engages the second transmission input 706 and operates the sampling device 714.

Referring now to FIGS. 9A to 9F, a mechanism that conforms to the descriptions of FIGS. 7A to 7C and 8A to 8C is illustrated. A pump 502, in the form of a syringe, has a piston 508 with a rack 510 which functions as a piston rod, forcing the piston 508. A screw gear 507 engages the rack 510 by means of an internal screw (not shown) to advance the rack 510 to the right. A rotary motor 500 drives a primary drive gear 506 through an output shaft 501. The primary drive gear 506 engages the screw gear 507 to move the rack 510 causing the pump 502 to generate a vacuum. The vacuum is conveyed by a tube 512, connected to a biopsy needle 524. The vacuum is channeled by the biopsy needle 524 to a sample chamber (not shown) near the tip 530 of the biopsy needle 524. The biopsy needle 524 has an outer sheath 526 and an inner sheath 532, which may be as described with reference to any of the embodiments described above. The outer sheath 526 is able to be rotated relative to the inner sheath 532 which is affixed to a housing 540 enclosing all of the components except distal portion 542 of the biopsy needle 524.

The rack 510 engages a pinion 514 which has a driving bevel gear 516 that engages a driven bevel gear 518. The driven bevel gear 518 is affixed to a sheath driving gear 520 which engages a sheath driven gear affixed concentrically to the outer sheath 526. The sample chamber is exposed, and a sample is cut, when an opening 528 in the outer sheath 526 is rotated by the sheath driven gear 522 at a point in time when the rack 510 engages the pinion 514.

Figure 9A:
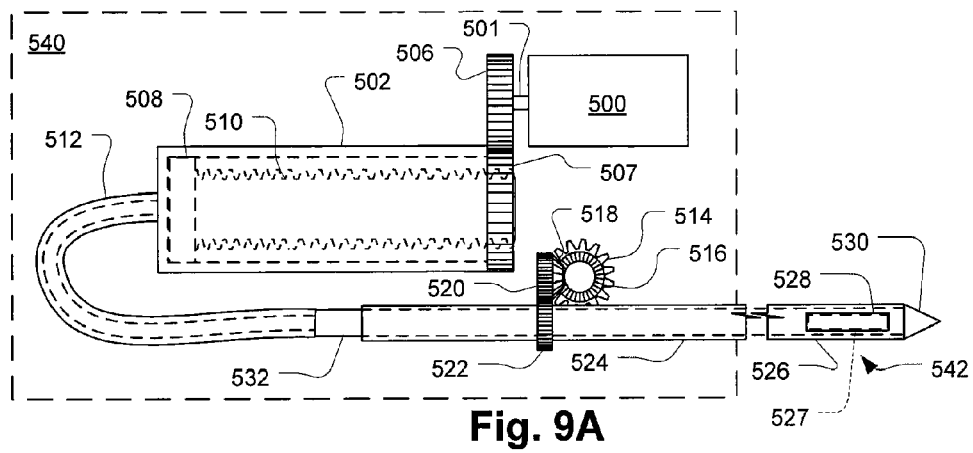
FIGS. 9A to 9F illustrate, respectively, a preferred embodiment of a biopsy needle and drive mechanism in several stages of an operating cycle.
Figure 9B:
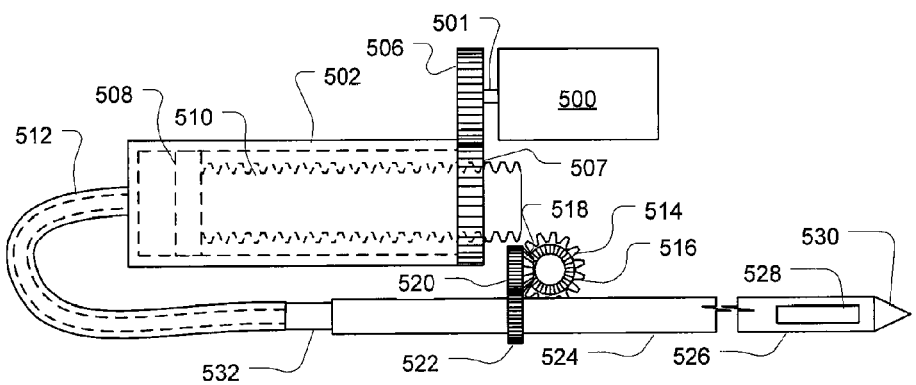
Figure 9C:
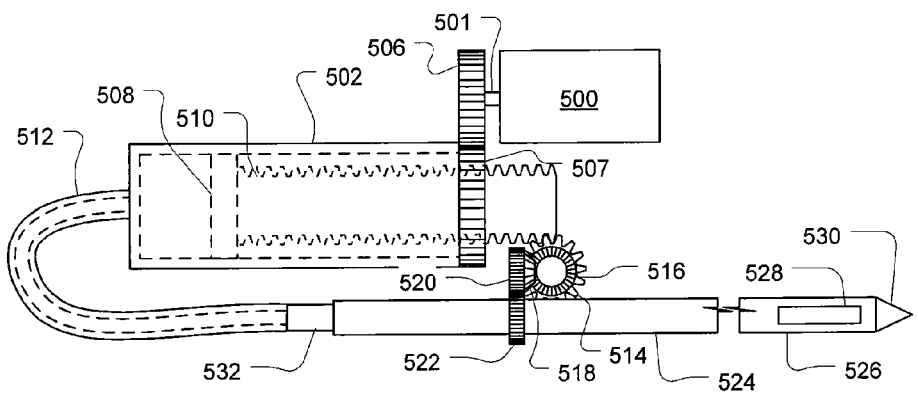
Figure 9D:
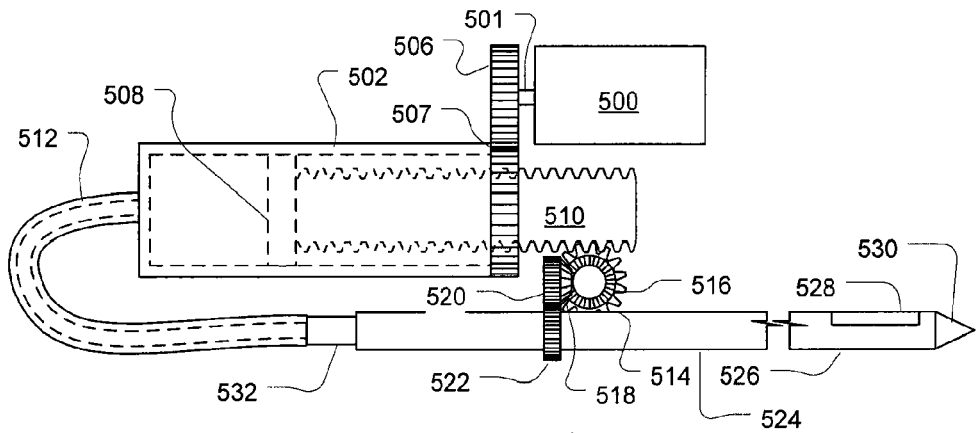
Figure 9E:
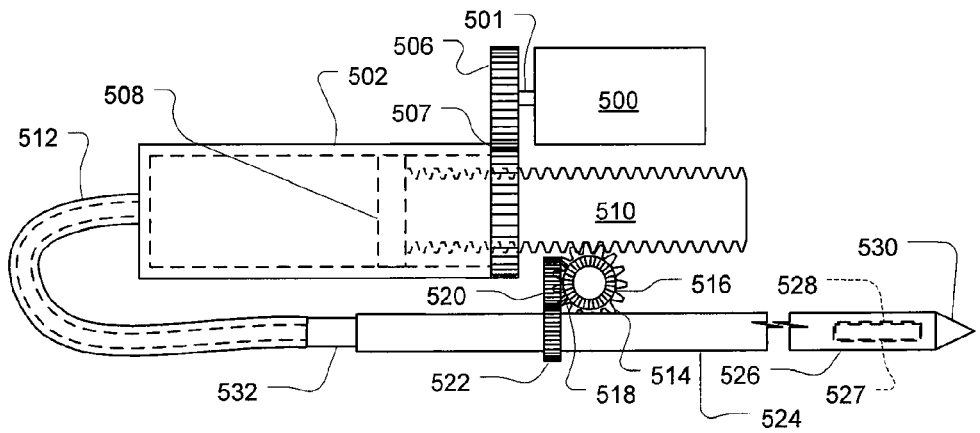
Figure 9F:
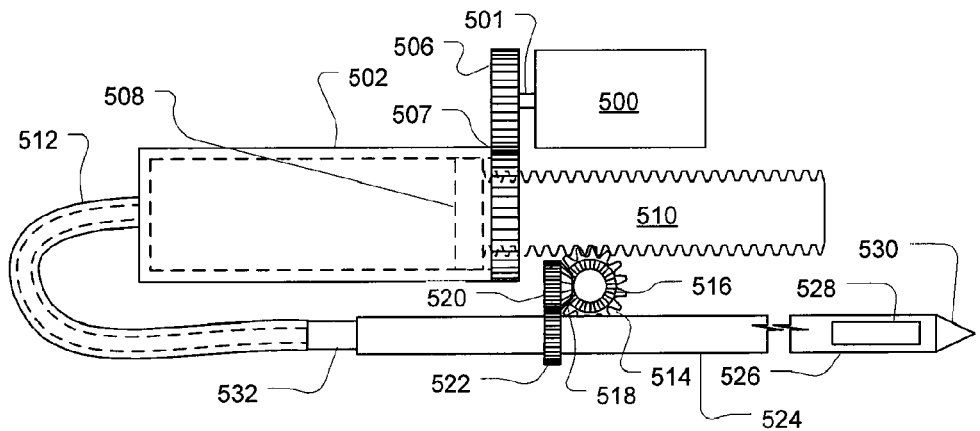
Figure 9G:
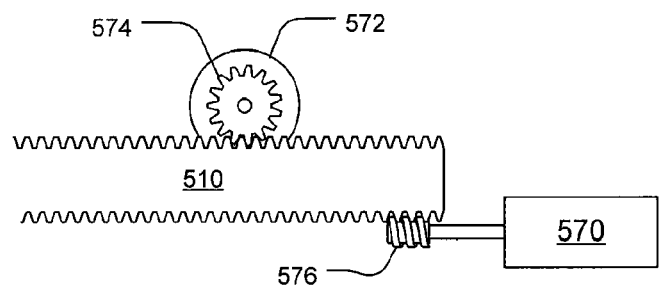
FIG. 9G shows alternative drives that may be used to a rack in various embodiments.

During a sampling procedure, the motor is run continuously in a single direction causing the rack 510 to advance to the right, driven by the screw gear 507. As the rack 510 moves to the right as illustrated in FIG. 9B, the piston 508 is also advanced, generating a partial vacuum. As the rack 510 moves further it reaches a point where it just engages the pinion 516 as shown in FIG. 9C. As the rack moves further still, as shown in FIG. 9D, the pinion is driven along with the rack 510 causing the vacuum to increase and the outer sheath 526 to begin rotating about the inner sheath 532. The rack continues to advance and, at a point illustrated in FIG. 9E, the inner sheath opening 527 and the outer sheath opening 528 are brought into coincidence thereby opening sample chamber and drawing in a sample due to the suction of the vacuum. The rack advances further (FIG. 9F) causing the sample to be cut placing the outer sheath 526 in a final position. As may be confirmed by inspection, the motor 500 may be operated in reverse to eject a sample by using the pump 502 to generate a pressure and force a tissue sample out of the sample chamber.

The mechanism used to displace the rack 510 can be any suitable mechanism. For example a pinion gear 574 may be used with a drive motor 572 which may itself include a gear train, such as a planetary gear, to amplify torque. Another example is a worm gear 576 as illustrated driven by a suitably arranged motor 570.

Referring now to FIG. 10A, another design for a biopsy device has a housing 605 that encloses most of the illustrated assembly, as shown. A motor 600 drives a drive gear 614 which meshes with a screw gear 615 which is internally threaded to engage and drive a threaded rod 608. The threaded rod 608 is attached to a piston 607 of a pump 602 which generates a vacuum in a tube 606. The tube 606 conveys the vacuum to a biopsy needle 618.

The biopsy needle 618 has an outer sheath 623 and an inner sheath 637. The outer sheath 623 rotates around the inner sheath 637 to bring an opening 620 in the outer sheath 623 into coincidence with an opening 621 in the inner sheath 637 and perform a cutting operation as the outer sheath. A pin 624 is affixed to the outer sheath 623 which can rotate around the inner sheath 637.

A pushrod 602 is connected to the threaded rod 608 and is open at the bottom to define a channel 604 so that the pushrod 602 can move without interfering with the tube 606. The pushrod displaces a cam drive 630 with a slot 631. The slot 631 has a helical portion 626 and a straight portion 638. A pin 624 is affixed to the outer sheath 623 and engaged in the slot 631. The cam drive 630 moves to the right as the piston 607 is displaced, the cam drive 630 being moved by the piston 607, threaded rod 608, pushrod 602, all of which move together. During an initial displacement of the piston 607, in which a vacuum is generated, the straight portion 638 of the slot 631 allows the cam drive 630 to move without affecting the position of the pin 624. When the helical portion 626 of the slot 631 reaches the pin 624, however, the outer sheath 623 is rotated as the piston 607 continues to be displaced. In this way, the cam drive 630 provides for an operation that is similar to that of FIGS. 9A to 9F.

Figure 11A:
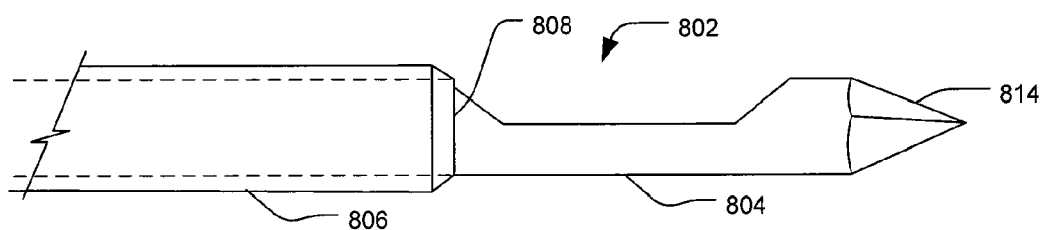
FIGS. 11A to 11C show a stylet and axial cutting sheath which may be used in embodiments of the invention.
Figure 11B:
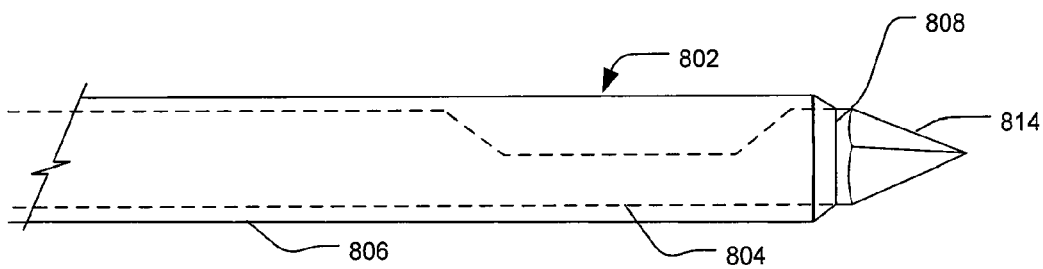
Figure 11C:
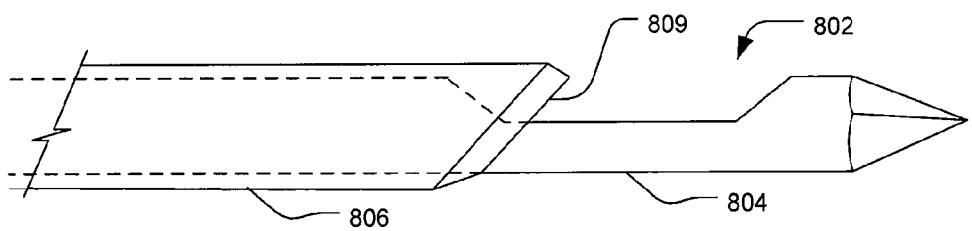

FIGS. 11A, 11B and 11C show a stylet 804 that has an axial cutting sheath 806 which may be used in embodiments of the invention. At the end of the stylet 804, a cutting tip 814 such as a trocar, may be provided. The axial cutting sheath 806 has a cutting edge 808 at a distal end which severs tissue samples from the host causing them to be deposited in a tissue basket 802 at the end of the stylet. At the same time, the cutting sheath 806 closes over the tissue basket 802, thereby enclosing it. Note that the relative sizes and proportions of the elements shown in FIGS. 11A and 11B are not essential features of the invention. Note also that the tissue basket 802 may be a hollow recess configured a manner similar to the embodiments of the figures discussed above. Known axially-displacing cutting sheaths rotate about the axis as they are displaced. In one embodiment, the cutting sheath is displaced with no, or nearly no, rotational motion. It is believed that for some kinds of tissue sampling, that this results in a higher quality sample, which may result from less rubbing of tissue sticking to a rotating cutting sheath.

FIGS. 12A to 12F show a biopsy needle embodiment for illustrating features including a linear actuator 901, an axial cutting sheath, and a spring-activated cutting action. A linear actuator 901 draws a shaft 903 attached to a piston 909 attached to a carriage 907 to generate a vacuum by expanding a volume 940 within a cylinder 905. An interior channel (not shown) of the stylet 931, which runs along its entire length of the stylet 931 from the hose 911 to the sample basket 915, is connected by a flexible hose 911 to the displaced volume 940. As the carriage 907 moves along the displacement interval between FIGS. 12A and 12B, the displaced volume 940 expands. This draws air through the hose 911, through the interior channel of the stylet 931, thereby creating a vacuum in a sample basket 915.

A pivot arm 933 is pivotally connected to the carriage 907 about a first end 939 thereof. A spring 943 generates a torque between a pivot arm 933 and a boss 905 on the carriage 907 to keep the free end 935 in engagement with a shelf 937. As the carriage 907 moves, rides along the shelf 937, from the position shown in FIG. 12A, until its free end 935 engages a catch plate 925 at the position shown in FIG. 12B. The catch plate 925 is affixed to a cutting sheath 913 which conforms to the description attending FIGS. 10A and 10B. A spring 921 connects the catch plate 925 and a boss 923, the boss 923 being fixed relative to the stylet 931. As the carriage 907 moves beyond the position of FIG. 12B toward the position of FIG. 12C, the cutting sheath 913 is retracted by the pivot arm 933 stretching the spring 921 thereby increasing a restoring force that urges the cutting sheath back toward a home position shown in FIG. 12A. As the cutting sheath 921 is retracted, the sample basket 915 is opened and the vacuum created in the sample basket 915 draws host tissue (not shown) into it.

Figure 12C:
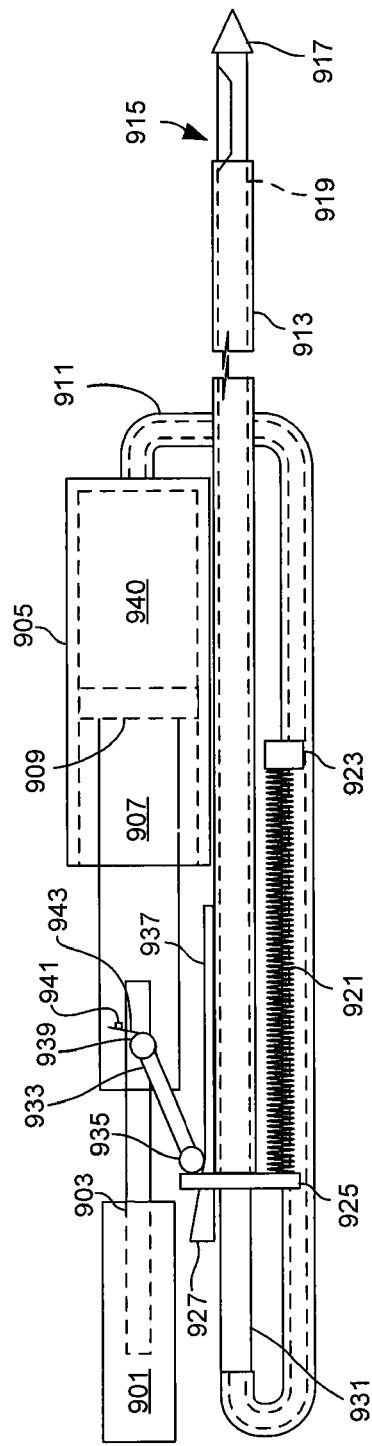
Figure 12D:
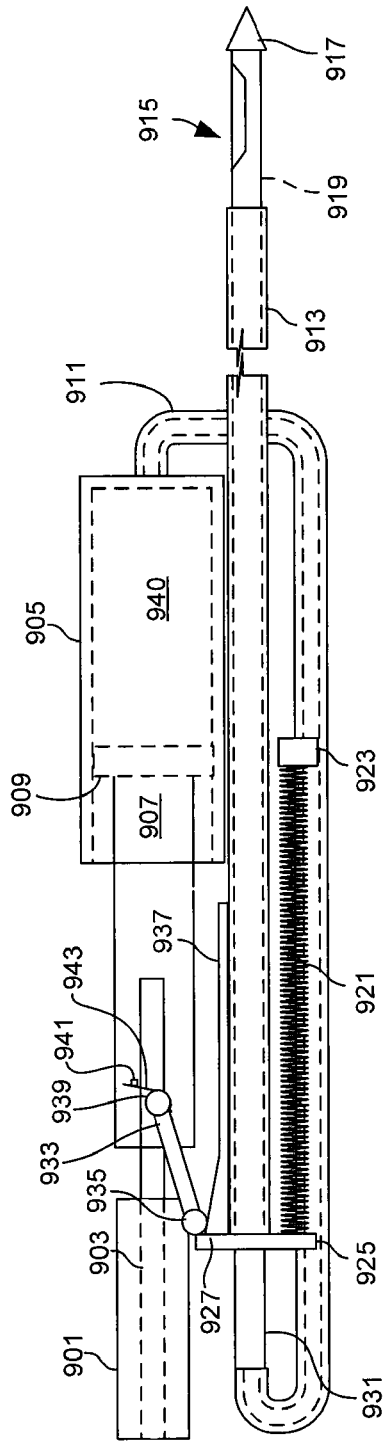
Figure 12E:
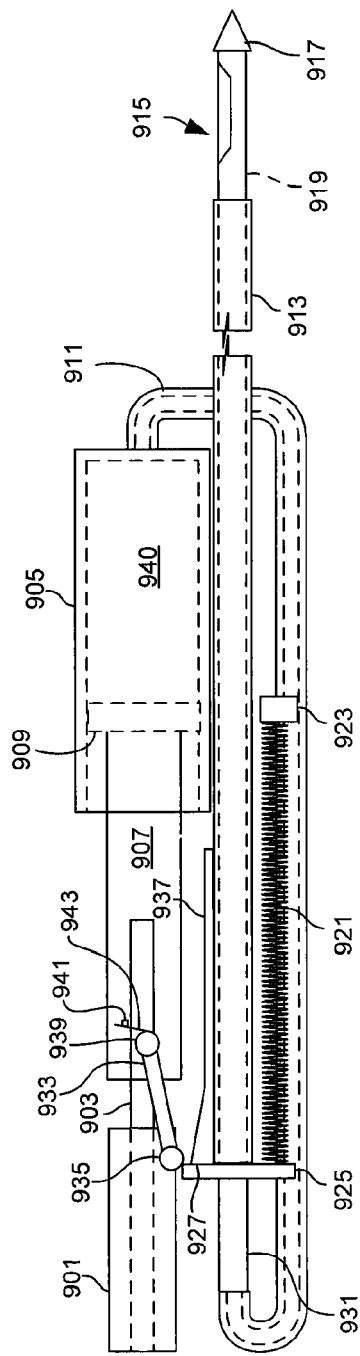
Figure 12F:
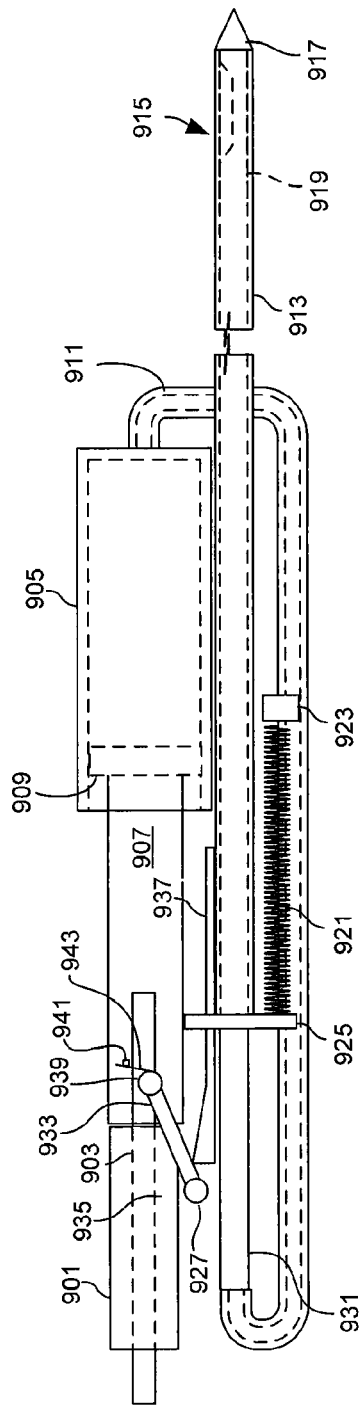

The cutting sheath 921 is further retracted as the carriage 907 moves further while the free end 935 slides up a ramp portion 927 of the shelf 937 as shown in FIG. 12D. At the same time, the cylinder 905 interior volume 940 continues to expand increasing or maintaining the vacuum in the sample basket 915. At the point shown in FIG. 12E, the free end 935 is moved to position in which it disengages from the catch plate 925 releasing the cutting sheath 913, thereby permitting the spring 921 to force it back to the home position of FIG. 12F. The displacement between the positions of FIGS. 12E and 12F causes a tissue sample to be severed by the movement of the cutting sheath 913. The carriage 907 may then be moved in an opposite direction to cause the free end 935 to return to a position in which it can retract the cutting sheath 913 again.

In any of the foregoing embodiments, the motors or prime movers disclosed in each embodiment may be replaced by rotary or linear motors which may be driven by electromotive force, by spring motors, hydraulic of pneumatic motors, thermal motors, or by any means of generating a motive force. Different types of displacement (e.g., rotary or linear) can be mapped to the required forms by means of suitable transmissions according to well-known techniques of kinematic design. For example, although the embodiment of FIGS. 12A to 12F shows a linear actuator 901, a drive such as the one shown in FIGS. 9A to 9F or 10A could be used as well. The linear actuator 901 may be a screw drive, an electronically controlled linear motor, a wax motor, a hydraulic or pneumatic motor, an artificial muscle or any suitable motor with a suitable kinematic mechanism to couple it to the cutting sheath and vacuum pump. In addition, although a syringe is preferred as a vacuum generating device, other types of vacuum generating devices may be employed in other embodiments of the invention, for example, a diaphragm pump, multiple-stroke positive displacement pump, screw pump, etc.

The above-disclosed embodiments may provide at least one of a variety of advantages including:
1. Substantial tissue sample-size can be recovered. For example, a 14 gauge needle with a suitably-sized sample opening, a 30 to 100 mg. tissue sample, and preferably a 50-60 mg. tissue sample, may be reliably recovered.
2. A single motor may be employed, according to some embodiments, to provide for vacuum and pressure generation, tissue sample cutting and recovery, etc.
3. The disclosed apparatuses and methods may provide a unitary disposable device or a unit with a disposable part and a re-usable part according to different embodiments. For example, the motor and part of the transmission, the housing and support elements may be provided in a durable component and the needle, vacuum generator, and other support elements may be provided in a disposable part.
4. The small number of elements, the power requirements, etc. are such that the biopsy needle may be provided in a lightweight and compact form making it easier to handle.
5. It is preferable for the biopsy device to have a center of gravity at its natural hand-hold position. The illustrated arrangements of elements makes it convenient for the biopsy device to be arrange for a housing to have a hand-grip that coincides with the center of gravity.

While the present invention has been disclosed with reference to certain preferred exemplary embodiments, numerous modifications, alterations, and changes to the described exemplary embodiments are possible without departing from the sphere and scope of the present invention. Accordingly, it is intended that the present invention not be limited to the described exemplary embodiments, but that it have the full scope.

The invention claimed is:

1. A method of operating a biopsy device in obtaining at least one tissue sample, comprising:
    inserting a sampling probe having a first component and a second component into a biological tissue mass, the first component and the second component being rotatable relative to each other, the first component having a sample chamber and a side port that opens to the sample chamber, and the second component having a side opening;
    generating a vacuum in the sample chamber during a first drive interval;
    rotating at least one of the first component and the second component of the sampling probe during a second drive interval until the side port of the first component and the side opening of the second component are in radial alignment; and
    rotating at least one of the first component and the second component of the sampling probe during a third drive interval to sever tissue drawn by vacuum into the sample chamber to deposit a tissue sample in the sample chamber.

2. The method of claim 1, wherein the first drive interval overlaps the second drive interval.

3. The method of claim 1, wherein the first drive interval overlaps the third drive interval.

4. The method of claim 1, comprising:
    generating a positive pressure in the sample chamber during a fourth drive interval; and
    rotating at least one of the first component and the second component of the sampling probe during a fifth drive interval until the side port of the first component and the side opening of the second component again are in radial alignment to release the positive pressure in the sample chamber to expel the tissue sample from the sample chamber.

5. The method of claim 4, wherein the fourth drive interval overlaps the fifth drive interval.

6. The method of claim 4, comprising operating a prime mover to drive a first transmission during the first drive interval to operate a pump to generate the vacuum in the sample chamber.

7. The method of claim 6, wherein the prime mover comprises a motor, and further comprising a controller configured to selectively operate the motor in forward and reverse directions.

8. The method of claim 6, comprising driving a second transmission during the second drive interval to rotate at least one of the first component and the second component of the sampling probe until the side port of the first component and the side opening of the component are in radial alignment.

9. The method of claim 8, wherein the first drive interval overlaps the second drive interval.

10. The method of claim 8, comprising driving the second transmission during the third drive interval to rotate at least one of first component and the second component of the sampling probe to sever tissue drawn by vacuum into the sample chamber.

11. The method of claim 10, wherein the first drive interval overlaps the third drive interval.

12. The method of claim 10, comprising operating the prime mover to drive the first transmission during the fourth drive interval to operate the pump to generate the positive pressure in the sample chamber.

13. The method of claim 12, comprising driving the second transmission during the fifth drive interval to rotate at least one of the first component and the second component of the sampling probe until the side port of the first component and the side opening of the second component again are in radial alignment to release the positive pressure in the sample chamber to expel the tissue sample from the sample chamber.

14. The method of claim 13, wherein the fourth drive interval overlaps the fifth drive interval.

15. A method for operating a biopsy device, comprising:
providing a biopsy needle having a first cylindrical member and a second cylindrical member, the first cylindrical member and the second cylindrical member being rotatable relative to each other, the first cylindrical member having a sample chamber and a side port that opens to the sample chamber, and the second cylindrical member having a side opening;
generating a vacuum in the sample chamber during a first drive interval;
rotating at least one of the first cylindrical member and the second cylindrical member of the biopsy needle during a second drive interval until the side port of the first cylindrical member and the side opening of the second cylindrical member are in radial alignment;
rotating at least one of the first cylindrical member and the second cylindrical member of the biopsy needle during a third drive interval to sever tissue drawn by vacuum into the sample chamber to deposit a tissue sample in the sample chamber;
generating a positive pressure in the sample chamber during a fourth drive interval; and
rotating at least one of the first cylindrical member and the second cylindrical member of the biopsy needle during a fifth drive interval until the side port of the first cylindrical member and the side opening of the second cylindrical member again are in radial alignment to release the positive pressure in the sample chamber to expel the tissue sample from the sample chamber.

16. The method of claim 15, wherein the first drive interval overlaps the second drive interval.

17. The method of claim 15, wherein the first drive interval overlaps the third drive interval.

18. The method of claim 15, wherein the fourth drive interval overlaps the fifth drive interval.

19. The method of claim 15, comprising operating a pump during the first drive interval to generate the vacuum in the sample chamber.

20. The method of claim 19, comprising operating the pump during the fourth drive interval to generate the positive pressure in the sample chamber.

* * * * *